US011696854B2

(12) United States Patent
Ray et al.

(10) Patent No.: US 11,696,854 B2
(45) Date of Patent: Jul. 11, 2023

(54) EARPLUG ASSEMBLY FOR IONTOPHORESIS SYSTEM

(71) Applicant: TUSKER MEDICAL, INC., Menlo Park, CA (US)

(72) Inventors: Miranda M. Ray, San Jose, CA (US); Rohit Girotra, San Francisco, CA (US); Anh Quoc Truong, San Jose, CA (US); Radhika Patel, Santa Rosa, CA (US); Thomas D. Gross, Los Gatos, CA (US); Alfredo Cantu, Pleasanton, CA (US)

(73) Assignee: TUSKER MEDICAL, INC., Menlo Park, CA (US)

( * ) Notice: Subject to any disclaimer, the term of this patent is extended or adjusted under 35 U.S.C. 154(b) by 409 days.

(21) Appl. No.: 17/063,115

(22) Filed: Oct. 5, 2020

(65) Prior Publication Data

US 2021/0015673 A1     Jan. 21, 2021

Related U.S. Application Data

(60) Continuation of application No. 16/028,687, filed on Jul. 6, 2018, now Pat. No. 10,842,676, which is a
(Continued)

(51) Int. Cl.
*A61F 11/20* (2022.01)
*A61F 11/00* (2022.01)
(Continued)

(52) U.S. Cl.
CPC ............ *A61F 11/202* (2022.01); *A61F 11/00* (2013.01); *A61M 31/00* (2013.01); *A61N 1/0428* (2013.01);
(Continued)

(58) Field of Classification Search
CPC ...... A61F 11/002; A61F 11/00; A61N 1/0526; A61N 1/0428; A61N 1/306; A61N 1/30; A61N 1/325; A61M 31/00
See application file for complete search history.

(56) References Cited

U.S. PATENT DOCUMENTS

| 858,673 A | 7/1907 | Roswell |
| 1,920,006 A | 7/1933 | Dozier et al. |
| (Continued) | | |

FOREIGN PATENT DOCUMENTS

| CA | 2424347 A1 | 10/2004 |
| CN | 86105171 A | 3/1987 |
| (Continued) | | |

OTHER PUBLICATIONS

JP OA for App No. 2018-500895 dated Nov. 25, 2020, 4 pages.
(Continued)

*Primary Examiner* — Bradley J Osinski
(74) *Attorney, Agent, or Firm* — Dickinson Wright PLLC

(57) ABSTRACT

An apparatus includes a rigid body, a flexible sealing element, a nozzle assembly, and an electrode. The rigid body defines a channel, a reservoir, and a vent path. The reservoir is in fluid communication with the channel. The vent path is in fluid communication with the reservoir. The reservoir is configured to provide spacing between the channel and the vent path. The sealing element is positioned distal to the rigid body. The nozzle assembly includes a nozzle head and a post. The post extends distally through the channel of the rigid body. The nozzle head projects distally from a distal end of the post. The electrode is disposed within the channel of the rigid body. The reservoir extends laterally from a longitudinal axis defined by the electrode.

14 Claims, 18 Drawing Sheets

Related U.S. Application Data division of application No. 14/800,869, filed on Jul. 16, 2015, now Pat. No. 10,016,304.

(51) Int. Cl.

| | | |
|---|---|---|
| *A61N 1/30* | (2006.01) | |
| *A61N 1/32* | (2006.01) | |
| *A61N 1/04* | (2006.01) | |
| *A61N 1/05* | (2006.01) | |
| *A61M 31/00* | (2006.01) | |

(52) U.S. Cl.
CPC ............. *A61N 1/0526* (2013.01); *A61N 1/30* (2013.01); *A61N 1/306* (2013.01); *A61N 1/325* (2013.01)

(56) References Cited

U.S. PATENT DOCUMENTS

| | | | |
|---|---|---|---|
| 2,458,884 | A | 1/1949 | Volkmann |
| 3,741,197 | A | 6/1973 | Sanz et al. |
| 3,888,258 | A | 6/1975 | Akiyama |
| 3,897,786 | A | 8/1975 | Garnett et al. |
| 3,913,584 | A | 10/1975 | Walchle et al. |
| 3,948,271 | A | 4/1976 | Akiyama |
| 3,991,755 | A | 11/1976 | Vernon et al. |
| 4,149,533 | A | 4/1979 | Ishikawa et al. |
| 4,206,756 | A | 6/1980 | Grossan |
| 4,406,282 | A | 9/1983 | Parker et al. |
| 4,468,218 | A | 8/1984 | Armstrong |
| 4,473,073 | A | 9/1984 | Darnell |
| 4,552,137 | A | 11/1985 | Strauss |
| 4,564,009 | A | 1/1986 | Brinkhoff |
| 4,601,294 | A | 7/1986 | Danby et al. |
| 4,712,537 | A | 12/1987 | Pender |
| 4,964,850 | A | 10/1990 | Bouton et al. |
| 4,968,296 | A | 11/1990 | Ritch et al. |
| 4,971,076 | A | 11/1990 | Densert et al. |
| 5,026,378 | A | 6/1991 | Goldsmith, III |
| 5,044,373 | A | 9/1991 | Northeved et al. |
| 5,047,007 | A | 9/1991 | McNichols et al. |
| 5,053,040 | A | 10/1991 | Goldsmith, III |
| 5,107,861 | A | 4/1992 | Narboni |
| 5,135,478 | A | 8/1992 | Sibalis |
| 5,160,316 | A | 11/1992 | Henley |
| 5,254,081 | A | 10/1993 | Maurer et al. |
| 5,254,120 | A | 10/1993 | Cinberg et al. |
| 5,261,903 | A | 11/1993 | Dhaliwal et al. |
| D352,780 | S | 11/1994 | Glaeser et al. |
| 5,421,818 | A | 6/1995 | Arenberg |
| 5,466,239 | A | 11/1995 | Cinberg et al. |
| 5,496,329 | A | 3/1996 | Reisinger |
| D378,611 | S | 3/1997 | Croley |
| 5,610,988 | A | 3/1997 | Miyahara |
| 5,643,280 | A | 7/1997 | Del Rio et al. |
| 5,674,196 | A | 10/1997 | Donaldson et al. |
| D387,863 | S | 12/1997 | Herman et al. |
| 5,707,383 | A | 1/1998 | Bays et al. |
| 5,792,100 | A | 8/1998 | Shantha |
| 5,804,957 | A | 9/1998 | Coln |
| 5,810,848 | A | 9/1998 | Hayhurst |
| 5,827,295 | A | 10/1998 | Del Rio et al. |
| 5,893,828 | A | 4/1999 | Uram |
| 5,979,072 | A | 11/1999 | Collins, II |
| D418,223 | S | 12/1999 | Phipps et al. |
| D420,741 | S | 2/2000 | Croley |
| 6,045,528 | A | 4/2000 | Arenberg et al. |
| D424,197 | S | 5/2000 | Sydlowski et al. |
| 6,059,803 | A | 5/2000 | Spilman |
| D426,135 | S | 6/2000 | Lee |
| 6,137,889 | A | 10/2000 | Shennib et al. |
| 6,148,821 | A | 11/2000 | Falco |
| 6,183,469 | B1 | 2/2001 | Thapliyal et al. |
| 6,200,280 | B1 | 3/2001 | Brenneman et al. |
| 6,206,888 | B1 | 3/2001 | Bicek et al. |
| 6,245,077 | B1 | 6/2001 | East et al. |
| 6,251,121 | B1 | 6/2001 | Saadat |
| 6,295,469 | B1 | 9/2001 | Linkwitz et al. |
| D450,843 | S | 11/2001 | McGuckin, Jr. et al. |
| 6,347,246 | B1 | 2/2002 | Perrault et al. |
| 6,358,231 | B1 | 3/2002 | Schindler et al. |
| 6,440,102 | B1 | 8/2002 | Arenberg et al. |
| 6,475,138 | B1 | 11/2002 | Schechter et al. |
| 6,512,950 | B2 | 1/2003 | Li et al. |
| 6,514,261 | B1 | 2/2003 | Randall et al. |
| 6,520,939 | B2 | 2/2003 | Lafontaine |
| 6,522,827 | B1 | 2/2003 | Loeb et al. |
| 6,553,253 | B1 | 4/2003 | Chang |
| 6,640,121 | B1 | 10/2003 | Telischi et al. |
| 6,645,173 | B1 | 11/2003 | Liebowitz |
| 6,648,873 | B2 | 11/2003 | Arenberg et al. |
| 6,663,575 | B2 | 12/2003 | Leysieffer |
| 6,682,558 | B2 | 1/2004 | Tu et al. |
| 6,770,080 | B2 | 8/2004 | Kaplan et al. |
| 6,916,159 | B2 | 7/2005 | Rush et al. |
| 7,123,957 | B2 | 10/2006 | Avrahami |
| 7,127,285 | B2 | 10/2006 | Henley et al. |
| 7,137,975 | B2 | 11/2006 | Miller et al. |
| D535,027 | S | 1/2007 | James et al. |
| 7,160,274 | B2 | 1/2007 | Ciok et al. |
| 7,344,507 | B2 | 3/2008 | Briggs et al. |
| 7,351,246 | B2 | 4/2008 | Epley |
| 7,381,210 | B2 | 6/2008 | Zarbatany et al. |
| D595,410 | S | 6/2009 | Luzon |
| 7,563,232 | B2 | 7/2009 | Freeman et al. |
| D598,543 | S | 8/2009 | Vogel et al. |
| 7,654,997 | B2 | 2/2010 | Makower et al. |
| 7,677,734 | B2 | 3/2010 | Wallace |
| 7,704,259 | B2 | 4/2010 | Kaplan et al. |
| 7,749,254 | B2 | 7/2010 | Sobelman et al. |
| D622,842 | S | 8/2010 | Benoist |
| 3,052,693 | A1 | 11/2011 | Shahoian |
| 8,192,420 | B2 | 6/2012 | Morriss et al. |
| 8,249,700 | B2 | 8/2012 | Clifford et al. |
| 8,409,175 | B2 | 4/2013 | Lee et al. |
| 8,425,488 | B2 | 4/2013 | Clifford et al. |
| 8,452,392 | B2 | 5/2013 | Morriss et al. |
| 8,498,425 | B2 | 7/2013 | Graylin |
| 8,518,098 | B2 | 8/2013 | Roeder et al. |
| 8,702,722 | B2 | 4/2014 | Shahoian |
| 8,840,602 | B2 | 9/2014 | Morriss et al. |
| 8,849,394 | B2 | 9/2014 | Clifford et al. |
| 9,011,363 | B2 | 4/2015 | Clopp et al. |
| 9,023,059 | B2 | 5/2015 | Loushin et al. |
| 9,216,112 | B2 | 12/2015 | Clifford et al. |
| 9,364,648 | B2 | 6/2016 | Girotra et al. |
| 9,387,124 | B2 | 7/2016 | Clifford |
| 9,392,229 | B2 | 7/2016 | Morriss et al. |
| 9,707,131 | B2 | 7/2017 | Shahoian |
| 9,713,710 | B2 | 7/2017 | Morriss et al. |
| 9,833,601 | B2 | 12/2017 | Clifford et al. |
| 9,950,157 | B2 | 4/2018 | Morriss et al. |
| 10,016,304 | B2 | 7/2018 | Ray et al. |
| 10,130,808 | B2 | 11/2018 | Kermani et al. |
| 10,195,369 | B2 | 2/2019 | Andreas et al. |
| 10,258,776 | B2 | 4/2019 | Clifford et al. |
| 10,478,344 | B2 | 11/2019 | Girotra et al. |
| 2002/0026125 | A1 | 2/2002 | Leysieffer |
| 2002/0069883 | A1 | 6/2002 | Hirchenbain |
| 2002/0111585 | A1 | 8/2002 | Lafontaine |
| 2002/0138091 | A1 | 9/2002 | Pflueger |
| 2002/0161379 | A1 | 10/2002 | Kaplan et al. |
| 2002/0169456 | A1 | 11/2002 | Tu et al. |
| 2003/0060799 | A1 | 3/2003 | Arenberg et al. |
| 2003/0093057 | A1 | 5/2003 | Zhang et al. |
| 2003/0120292 | A1 | 6/2003 | Park et al. |
| 2003/0199791 | A1 | 10/2003 | Boecker et al. |
| 2004/0054339 | A1 | 3/2004 | Ciok et al. |
| 2005/0094835 | A1 | 5/2005 | Doty |
| 2005/0154357 | A1 | 7/2005 | Pinel |
| 2005/0182385 | A1 | 8/2005 | Epley |
| 2005/0203552 | A1 | 9/2005 | Laufer et al. |
| 2005/0235422 | A1 | 10/2005 | Wallace |
| 2005/0240147 | A1 | 10/2005 | Makower et al. |

(56) References Cited

U.S. PATENT DOCUMENTS

| | | |
|---|---|---|
| 2005/0284479 A1 | 12/2005 | Schrader et al. |
| 2006/0079957 A1 | 4/2006 | Chin et al. |
| 2006/0142700 A1 | 6/2006 | Sobelman et al. |
| 2006/0155304 A1 | 7/2006 | Kaplan et al. |
| 2006/0177080 A1 | 8/2006 | Smith |
| 2007/0003096 A1 | 1/2007 | Nam |
| 2007/0066946 A1 | 3/2007 | Haggstrom et al. |
| 2007/0078372 A1 | 4/2007 | Reddy et al. |
| 2007/0183613 A1 | 8/2007 | Juneau et al. |
| 2007/0233222 A1 | 10/2007 | Roeder et al. |
| 2008/0011308 A1 | 1/2008 | Fleming |
| 2008/0051804 A1 | 2/2008 | Cottler et al. |
| 2008/0058756 A1 | 3/2008 | Smith |
| 2008/0065002 A1 | 3/2008 | Lobl et al. |
| 2008/0107287 A1 | 5/2008 | Beard |
| 2008/0212416 A1 | 9/2008 | Polonio et al. |
| 2008/0262468 A1 | 10/2008 | Clifford et al. |
| 2008/0262508 A1 | 10/2008 | Clifford et al. |
| 2008/0262510 A1 | 10/2008 | Clifford |
| 2009/0163848 A1 | 6/2009 | Morriss et al. |
| 2009/0209972 A1 | 8/2009 | Loushin et al. |
| 2009/0262510 A1 | 10/2009 | Pekkarinen et al. |
| 2009/0270807 A1 | 10/2009 | Mas et al. |
| 2009/0299344 A1 | 12/2009 | Lee et al. |
| 2010/0030131 A1 | 2/2010 | Morriss et al. |
| 2010/0041447 A1 | 2/2010 | Graylin |
| 2010/0061581 A1 | 3/2010 | Soetejo et al. |
| 2010/0198135 A1 | 8/2010 | Morriss et al. |
| 2010/0300460 A1 | 12/2010 | Falco et al. |
| 2011/0001564 A1 | 1/2011 | Hori |
| 2011/0015645 A1 | 1/2011 | Liu et al. |
| 2011/0048414 A1 | 3/2011 | Hoekman et al. |
| 2011/0268303 A1 | 11/2011 | Ahsani |
| 2011/0288559 A1 | 11/2011 | Shahoian |
| 2012/0109070 A1 | 5/2012 | Elsamahy et al. |
| 2012/0310145 A1 | 12/2012 | Clifford et al. |
| 2013/0090544 A1 | 4/2013 | Clifford et al. |
| 2013/0190678 A1 | 7/2013 | Andreas et al. |
| 2013/0197426 A1 | 8/2013 | Morriss et al. |
| 2013/0223702 A1 | 8/2013 | Holsing et al. |
| 2014/0102461 A1* | 4/2014 | Girotra .............. A61F 11/08 128/864 |
| 2014/0194891 A1 | 7/2014 | Shahoian |
| 2014/0276352 A1 | 9/2014 | Kermani et al. |
| 2014/0276906 A1 | 9/2014 | Andreas et al. |
| 2015/0068539 A1 | 3/2015 | Morriss et al. |
| 2016/0361204 A1 | 12/2016 | Girotra et al. |
| 2016/0375204 A1 | 12/2016 | Andreas et al. |
| 2017/0014272 A1 | 1/2017 | Ray et al. |
| 2017/0028193 A1 | 2/2017 | Morriss et al. |
| 2018/0085563 A1 | 3/2018 | Clifford et al. |
| 2018/0256894 A1 | 9/2018 | Morriss et al. |
| 2018/0304059 A1 | 10/2018 | Clifford et al. |
| 2019/0083780 A1 | 3/2019 | Kermani et al. |
| 2019/0298940 A1 | 10/2019 | Andreas et al. |

FOREIGN PATENT DOCUMENTS

| | | |
|---|---|---|
| CN | 2087067 U | 10/1991 |
| CN | 2409940 Y | 12/2000 |
| CN | 203898546 U | 10/2014 |
| DE | 19618585 A1 | 11/1997 |
| EP | 0214527 A1 | 3/1987 |
| FR | 2526656 A1 | 11/1983 |
| JP | S59129815 U | 8/1984 |
| JP | H07116190 A | 5/1995 |
| JP | 2010524584 A | 7/2010 |
| WO | 9210223 A1 | 6/1992 |
| WO | 1992010223 A1 | 6/1992 |
| WO | 1999017825 A1 | 4/1999 |
| WO | 2002043795 A1 | 6/2002 |
| WO | 2006119512 A2 | 11/2006 |
| WO | 2008030485 A2 | 3/2008 |
| WO | 2008036368 A2 | 3/2008 |
| WO | 2008131195 A2 | 10/2008 |
| WO | 2009010788 A1 | 1/2009 |
| WO | 2010014894 A1 | 2/2010 |
| WO | 2011081772 A1 | 7/2011 |
| WO | 2013016098 A2 | 1/2013 |
| WO | 2013181009 A1 | 12/2013 |
| WO | 2014158543 A1 | 10/2014 |
| WO | 2017011777 A1 | 1/2017 |

OTHER PUBLICATIONS

AU Office Action for App No. 2016291677 dated May 13, 2020; 7 pages.
CN Office Action for Patent Application No. 2016800495548; 9 pages.
JP Office Action for Patent Application No. 2018-500895 dated Jun. 12, 2020; 4 pages.
First Office Action for Chinese Application No. 201680049554.8, dated Sep. 19, 2019; 19 pages.
U.S. Appl. No. 60/912,902, filed Apr. 19, 2007.
Patent Examination Report No. 1 for Australian Patent Application No. 2008242735, dated Aug. 8, 2012; 3 pages.
Patent Examination Report No. 1 for Australian Patent Application No. 2013209354, dated Oct. 13, 2014; 5 pages.
First Office Action for Chinese Patent Application No. 200880020861.9, dated Jul. 12, 2011; 10 pages.
Second Office Action for Chinese Patent Application No. 20080020861.9, dated Dec. 31, 2011; 3 pages.
Search Report for Chinese Patent Application No. 20130047126.X, dated Mar. 6, 2015; 2 pages.
Second Office Action for Chinese Patent Application No. 20130047126.X, dated Mar. 16, 2015; 10 pages.
Office Action for European Application No. 08746237.0, dated Mar. 24, 2016; 3 pages.
Office Action for European Application No. 08746237.0, dated Aug. 4, 2015; 7 pages.
Supplementary Partial Search Report for European Application No. 08746237.0, dated Jun. 30, 2014; 9 pages.
Notification of Reasons for Refusal for Japanese Patent Application No. 2010-504267, dated Nov. 20, 2012; 4 pages.
Notification for Reason for Refusal for Japanese Aptent Applicaton No. 2010-504267, dated Nov. 12, 2013; 4 pages.
International Search Report for International Application No. PCT/US2008.060779, dated Sep. 3, 2008.
Written Opinion for International Application No. PCT.US2008/060779, dated Sep. 3, 2008.
Office Action for U.S. Appl. No. 11/749,733, dated Jun. 10, 2009; 13 pages.
Office Action for U.S. Appl. No. 11/749,733, dated Dec. 2, 2008; 9 pages.
U.S. Appl. No. 61/085,360, filed Jul. 31, 2008.
Patent Examination Report No. 1 for Australian Applicatin No. 2009276384, dated Apr. 14, 2014; 3 pages.
Office Action for Canadian Application No. 2,732,595, dated Dec. 8, 2015; 4 pages.
Office Action for Russian Application No. 2011-07228, dated May 24, 2013.
International Search Report for International Application No. PCT/US2009/052395, dated Nov. 6, 2009.
Written Opinion for International Application No. PCT/US2009/052395, dated Nov. 6, 2009.
Patent Examination Reprot No. 1 for Australian Applicaton No. 2010337214, dated Feb. 27, 2015; 3 pages.
Office Action for Chinese Application No. 201080065012.2, dated Mar. 31, 2016; 20 pages.
International Search Report and Written Opinion for International Application No. PCT/US2010058718, dated Feb. 17, 2011; 12 pages.
International Search Report and Written Opinion for International Application No. PCT/US2010/042128, dated Aug. 27, 2010; 10 pages.
Office Action for Australian Application No. 2012287268, dated Feb. 11, 2016.

(56) References Cited

OTHER PUBLICATIONS

Office Action for European Application No. 12743007.2, dated Jul. 21, 2016; 5 pages.
Notification of Reasons for Refusal for Japanese Application No. 2014-522882, dated May 31, 2016.
International Search Report and Written Opinion for International Application No. PCT/US2012/047179, dated Mar. 11, 2013; 15 pages.
First Office Action for Chinese Patent Application No. 201380027926.3, dated May 3, 2016.
International Search Report and Written Opinion for International Applicatin No. PCT/US2013/041816, dated Sep. 16, 2013; 14 pages.
International Search Report and Written Opinion for International Application No. PCT/US2014/018017, dated May 22, 2014; 12 pages.
Office Action for U.S. Appl. No. 14/800,869, dated Aug. 24, 2017; 11 pages.
International Search Report and Written Opinion for International Application No. PCT/US2016/042577, dated Dec. 6, 2016; 14 pages.
International Search Report and Written Opinion for International Application No. PCT/US2009/069388, dated Jun. 30, 2010; 16 pages.
Comeau, M. et al., "Local anesthetisa of the Ear by Iontophoresis," vol. 98, Arch. Otolaryngol., pp. 114-120 (Aug. 1973).
Comeau, M. et al., "Anesthesia of the Human Tympanic Membrane by Iontophoresis of a Local Anesthetic," The Larynogoscope, vol. 88, pp. 277-285 (1978).
Echols, D.F. et al., "Anesthesia of the Ear by Iontophoresis of Lidocaine," Arch. Otolaryngol., vol. 101, pp. 418-421 (Jul. 1975).
Epley, J.M., "Modified Technique of Iontophoretic Anesthesia for Myringotomy in Children," Arch. Otolaryngol., vol. 103, pp. 358-360 (Jun. 1977).
Hasegawa, M. et al., "Iontophoretic anaesthesia of the tympanic membrae," Clinical Otolaryngoloy, vol. 3, pp. 63-66 (1978).
Ramsden, R.T. et al., "Anaesthesia of the tympanic membrane using iontophoresis," The Journal of Laryngology and Otology, 56(9): 779-785 (Sep. 1977).
"Definition of Plenum," Compact Oxford English Dictionary (online), Retrieved from the Internet: <hhtp://oxforddictionaries.com/definition/english/plenum>, Retrieved on Aug. 14, 2012, 1 page.
Medtronic XOMED, "Activent Antimicrobial Ventilation Tubes," Rev.1.1, pp. 1-4, 2002, Jacksonville, FL.
Micomedics Innovative Surgical Products, "Micromedics Tympanostomy Tubes," (online), Relieved on Jul. 15, 2010, retrivd from the internet <URL: http://www.micromedics-usa.com/products/otology/micromedicstubes.htm>, 7 pages.
Second Office Action for Chinese Patent Application No. 200880020861.9, dated Dec. 31, 2011, 3 pages.
Search Report for Chinese Patent Application No. 201310047126.X, dated Mar. 6, 2015, 2 pages.
Second Office Action for Chinese Patent Application No. 201310047126.X, dated Mar. 16, 2015, 10 pages.
Notification of Reasons for Refusal for Japanese Patent Application No. 2010-504267, dated Nov. 12, 2013, 4 pages.
Patent Examination Report No. 1 for Austrailian Application No. 2009276384, dated Apr. 14, 2014, 3 pages.
Patent Examination Report No. 1 for Australian Application No. 2010337214, dated Feb. 27, 2015, 3 pages.
International Search Report for International Application No. PCT/US2010/058718, dated Feb. 17, 2011.
Written Opinion for International Application No. PCT/US2010/058718, dated Feb. 17, 2011.
International Search Report for International Application No. PCT/US2010/042128, dated Aug. 27, 2010.
International Search Report for International Application No. PCT/US2012/047179, dated Mar. 11, 2013.
Written Opinion for International Application No. PCT/US2012/047179, dated Mar. 11, 2013.
International Search Report for International Application No. PCT/US2013/041816, dated Sep. 16, 2013, 7 pages.
Written Opinion for International Application No. PCT/US2013/041816, dated Sep. 16, 2013, 7 pages.
International Search Report for International Application No. PCT/US2009/069388, dated Jun. 30, 2010.
Comeau, M. et al., "Local Anesthesia of the Ear by Iontophoresis," vol. 98, Arch. Otolaryngol., pp. 114-120 (Aug. 1973).
Comeau, M. et al., "Anesthesia of the Human Tympanic Membrane by Iontophoresis of a Loval Anesthetic," The Larynogoscope, vol. 88, pp. 277-285 (1978).
Epley, J. M., "Modified Technique of Iontophoretic Anesthesia for Myringotomy in Children," Arch. Otolaryngol., vol. 103, pp. 358-360 (Jun. 1977).
Hasegawa, M. et al., "Iontophorectic anaesthesia of the tympanic membrane," Clinical Otolaryngoloy, vol. 3, pp. 33-66 (1978).
Ramsden, R. T. et al., "Anaesthesia of the tympanic membraine using iontophoresis," The Journal of Laryngology and Otology, 56(9): 779-785 (Sep. 1977).
"Definition of Plenum," Compact Oxford English Dictionary [online], Retrieved from the Internet: <http://oxforddictionaries.com/definition/english/plenum>, Retrieved on Aug. 6, 2012, 2 pages.
Definition of Plenum,: Merriam-Webster's Online Dictionary, 11th Edition [online], Retrieved from the Internet: <http://www.merriam-webster.com/dictionary/plenum>, Retrieved on Aug. 14, 2012, 1 page.
Micromedics Innovative Surgical Products, "Micromedics Tympanostomy Tubes," [online], Retrieved on Jul. 15, 2010, Retrieved from the Internet <URL: http://www.micromedics-usa.com/products/otology/micromedicstubes.htm>, 7 pages.

\* cited by examiner

EARPLUG ASSEMBLY FOR IONTOPHORESIS SYSTEM

CROSS-REFERENCE TO RELATED APPLICATIONS

This application is a continuation of U.S. application Ser. No. 16/028,687 filed Jul. 6, 2018 titled "Earplug Assembly for Iontophoresis System" (now U.S. Pat. No. 10,842,676) which is a divisional of and claims priority to U.S. patent application Ser. No. 14/800,869, filed Jul. 16, 2015 and also titled "Earplug Assembly for Iontophoresis System" (now U.S. Pat. No. 10,016,304). Both applications are incorporated herein by reference as if reproduced in full below.

BACKGROUND

Some children may exhibit recurrent episodes of otitis media and/or -otitis media with effusion. Treatment of severe cases may involve the placement of a pressure equalization tube or tympanostomy tube through the tympanic membrane to provide adequate drainage of the middle ear by providing fluid communication between the middle and outer ear. In particular, such a tube may provide a vent path that promotes drainage of fluid from the middle ear via the Eustachian tube and may thus reduce stress imposed on the tympanic membrane from pressure within the middle ear. This may further reduce the likelihood of future infections and pressure induced ruptures of the tympanic membrane. Pressure equalization tubes may fall out spontaneously within about a year of placement. Exemplary pressure equalization tube delivery systems are disclosed in U.S. Pat. No. 8,052,693, entitled "System and Method for the Simultaneous Automated Bilateral Delivery of Pressure Equalization Tubes," issued Nov. 8, 2011, the disclosure of which is incorporated by reference herein. Additional exemplary pressure equalization tube delivery systems are disclosed in U.S. Pat. No. 8,249,700, entitled "System and Method for the Simultaneous Bilateral Integrated Tympanic Drug Delivery and Guided Treatment of Target Tissues within the Ears," issued Aug. 21, 2012, the disclosure of which is incorporated by reference herein. Still additional exemplary pressure equalization tube delivery systems are disclosed in U.S. Pub. No. 2011/0015645, entitled "Tympanic Membrane Pressure Equalization Tube Delivery System," published Jan. 20, 2011, the disclosure of which is incorporated by reference herein.

Insertion of a pressure equalization tube may be performed using general anesthesia in some cases, which may require additional resources such as an operating room, the presence of an anesthesiologist, and time in a recovery room. Furthermore, the use of general anesthesia may include certain risks that a patient may or may not be comfortable with undertaking. Some pressure equalization tube delivery systems and methods provide a local anesthetic through iontophoresis. Examples of such systems and methods are disclosed in U.S. Pub. No. 2010/0198135, entitled "Systems and Methods for Anesthetizing Ear Tissue," published Aug. 5, 2010, the disclosure of which is incorporated by reference herein. Additional examples of such systems and methods are disclosed in U.S. Pat. No. 8,192,420, entitled "Iontophoresis Methods," issued Jun. 5, 2012, the disclosure of which is incorporated by reference herein.

While a variety of pressure equalization tube delivery systems and methods have been made and used, it is believed that no one prior to the inventor(s) has made or used an invention as described herein.

BRIEF DESCRIPTION OF THE DRAWINGS

It is believed the present invention will be better understood from the following description of certain examples taken in conjunction with the accompanying drawings, in which like reference numerals identify the same elements and in which.

Figure 1:
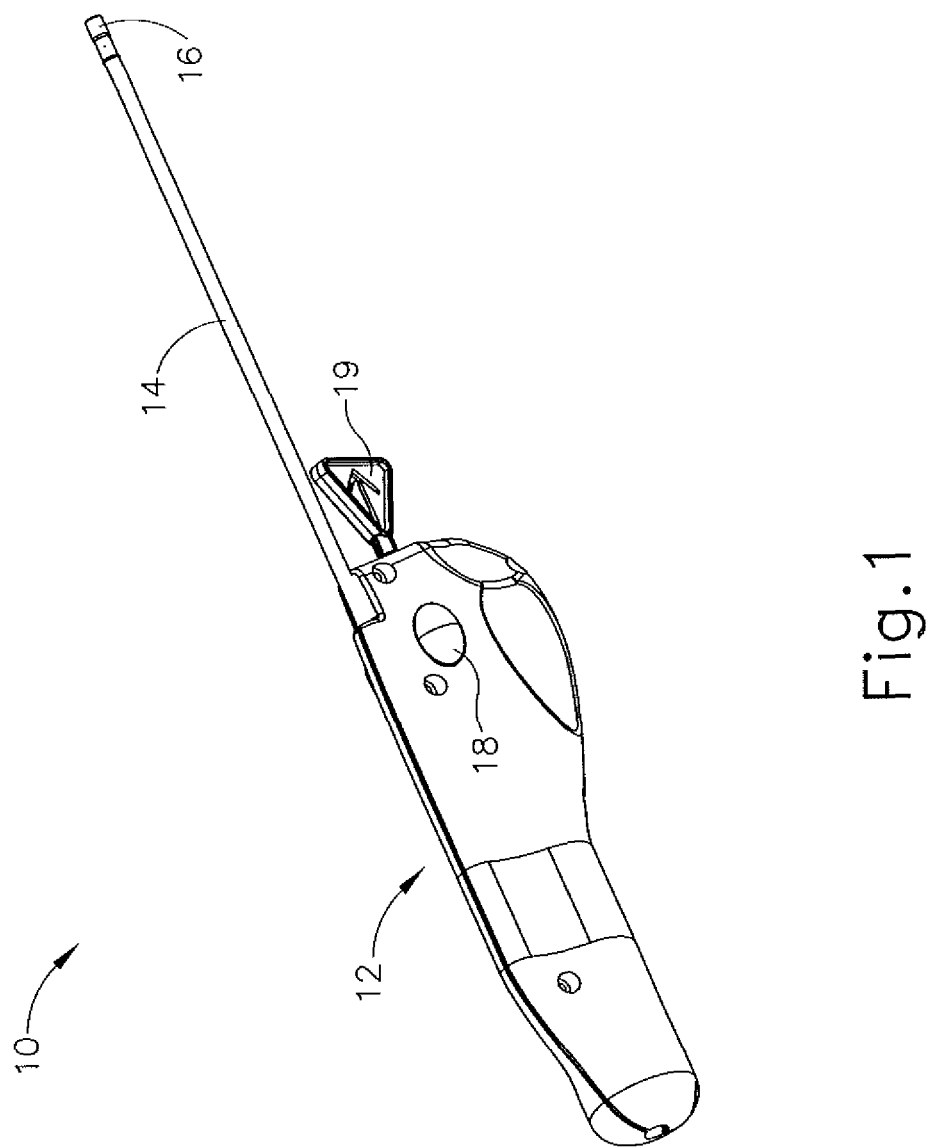
FIG. 1 depicts a perspective view of an exemplary pressure equalization tube delivery device (PETDD)

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. EXEMPLARY PRESSURE EQUALIZATION TUBE DELIVERY DEVICE (PETDD)

As noted above, a pressure equalization (PE) tube may be delivered to the tympanic membrane (TM) of a patient as a way of treating, for example, otitis media. In some instances, a delivery instrument may be used to insert PE tubes in the tympanic membrane (TM) without the use of general anesthesia. FIG. 1 shows an exemplary equalization tube delivery device (PETDD) (10) that may be used in such procedures. It should be understood that PETDD (10) may be used with an endoscope to provide visualization of the tympanic membrane (TM) during use of PETDD (10). It should also be understood that a patient may receive local anesthesia at the tympanic membrane (TM) through a process of iontophoresis before PETDD (10) is actuated to deploy a PE tube. Various examples of devices and methods that may be used to provide iontophoresis will be described in greater detail below. It should also be understood that iontophoresis may be provided in accordance with at least some of the teachings of U.S. Pub. No. 2010/0198135, the disclosure of which is incorporated by reference herein; and/or in accordance with at least some of the teachings of U.S. Pat. No. 8,192,420, the disclosure of which is incorporated by reference herein.

As shown in FIG. 1, PETDD (10) of this example includes a handpiece (12) and a cannula (14) extending distally from handpiece (12). Cannula (14) is sized for insertion in a patient's ear canal, such that the tip (16) of cannula may directly engage the patient's tympanic membrane (TM). As soon as the tip (16) achieves apposition with the tympanic membrane (TM), the operator may depress button (18), which may trigger a firing sequence whereby PETDD (10) creates a myringotomy incision, dilates the myringotomy incision, and inserts a PE tube in the myringotomy incision nearly instantly. A pin (19) selectively locks button (18) to avoid premature firing of PETDD (10), such that the operator must remove pin (19) before intentionally firing PETDD (10).

By way of example only, PETDD (10) may be constructed and operable in accordance with at least some of the teachings of U.S. Pat. No. 8,052,693, the disclosure of which is incorporated by reference herein; U.S. Pat. No. 8,249,700, the disclosure of which is incorporated by reference herein; U.S. Pub. No. 2011/0015645, the disclosure of which is incorporated by reference herein; and/or U.S. Pub. No. 2014/0276906, entitled "Features to Improve and Sense Tympanic Membrane Apposition by Tympanostomy Tube Delivery Instrument," filed on even date herewith, the disclosure of which is incorporated by reference herein. Other suitable forms that PETDD (10) may take will be apparent to those of ordinary skill in the art in view of the teachings herein. It should also be understood that a PE tube may be inserted in a tympanic membrane (TM) manually, such as by creating the myringotomy incision with a knife and inserting the PE tube using forceps, etc.

Figure 2:
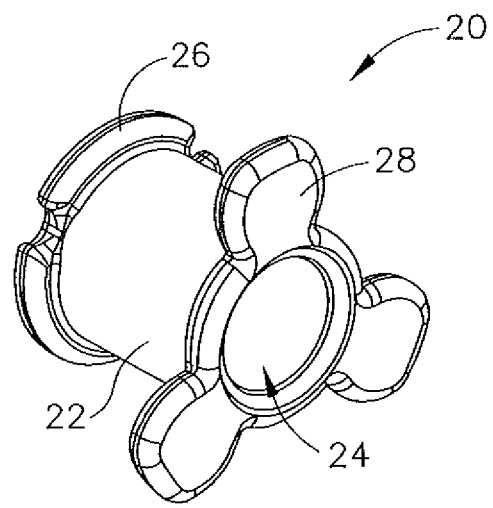
FIG. 2 depicts a perspective view of an exemplary pressure equalization (PE) tube suitable for delivery by the PETDD of FIG. 1.
Figure 3:
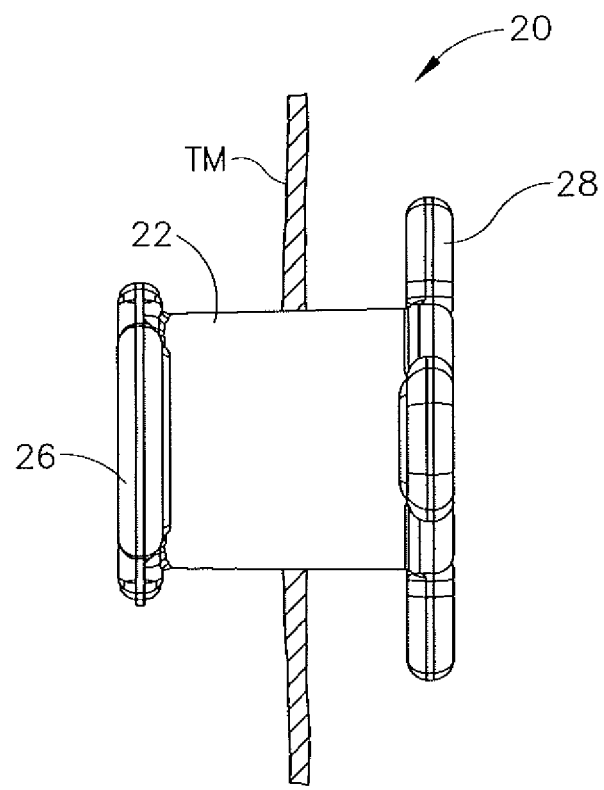
FIG. 3 depicts a side elevational view of the PE tube of FIG. 2, positioned within a tympanic membrane.

FIGS. 2-3 show an exemplary PE tube (20) that may be delivered to the tympanic membrane (TM) using PETDD (10). PE tube (20) of this example comprises a cylindraceous body (22) that defines a passageway (24). A flange (26) is located at one end of body (22) while a set of petals (28) are located at the other end of body (22). PE tube (20) is formed of a resilient material that is biased to assume the rivet like configuration shown in FIGS. 2-3. However, flange (26) and petals (28) may be flexed inwardly toward the longitudinal axis of body (22) to provide PE tube (20) with a cylindraceous configuration. In particular, flange (26) and petals (28) may be flexed such that their outer surfaces are at the same radial distance from the longitudinal axis as the outer perimeter of body (22). This may enable PE tube (200) to collapse to fit within cannula (14). When PE tube (20) is disposed in a tympanic membrane (TM), petals (28) are located medially (i.e., on the middle ear side) while flange (26) is located laterally (i.e., on the outer ear side).

By way of example only, PE tube (20) may also be configured in accordance with at least some of the teachings of U.S. Pat. No. 9,011,363, entitled "Tympanic Membrane Pressure Equalization Tube," issued Apr. 21, 2015, the disclosure of which is incorporated by reference herein; and/or at least some of the teachings U.S. Pub. No. 2014/0276906, the disclosure of which is incorporated by reference herein. Other suitable forms that PE tube (20) may take will be apparent to those of ordinary skill in the art in view of the teachings herein.

II. EXEMPLARY IONTOPHORESIS SYSTEM

As noted above, PETDD (10) may be used in conjunction with an iontophoresis system, which may be used to anesthetize the patient's ear before PETDD (10) is inserted into the patient's ear canal to deliver PE tube (20) in the tympanic membrane (TM). By way of example only, iontophoresis may be provided in accordance with at least some of the teachings of U.S. Pub. No. 2010/0198135, the disclosure of which is incorporated by reference herein; and/or in accordance with at least some of the teachings of U.S. Pat. No. 8,192,420, the disclosure of which is incorporated by reference herein. In addition or in the alternative, iontophoresis may be provided in accordance with any of the various teachings below. It should be understood that any of the below teachings may be readily combined with at least some of the teachings of U.S. Pub. No. 2010/0198135, the disclosure of which is incorporated by reference herein; and/or at least some of the teachings of U.S. Pat. No. 8,192,420, the disclosure of which is incorporated by reference herein.

Figure 4:
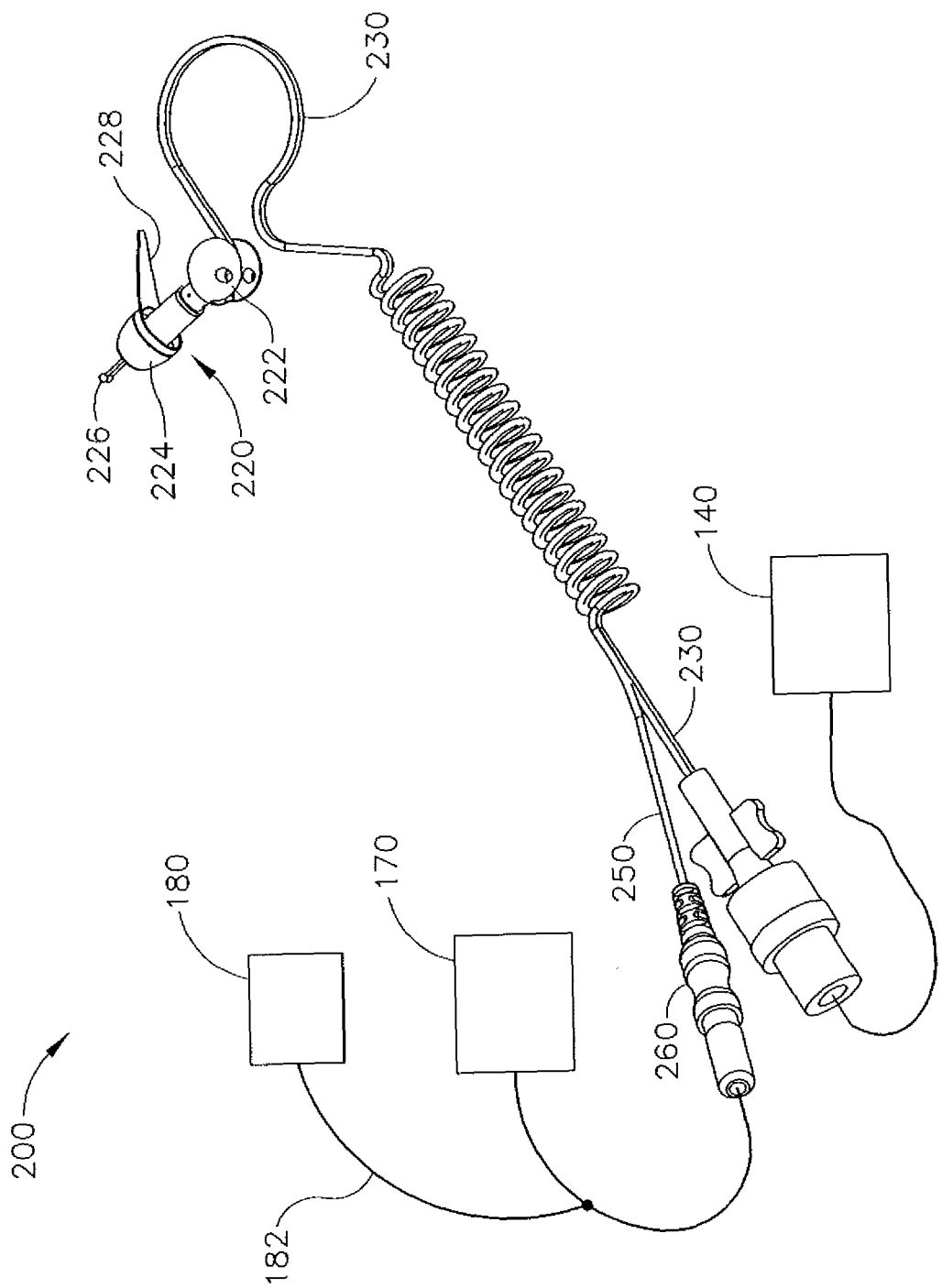
FIG. 4 depicts an exemplary iontophoresis system incorporating an earplug.

FIG. 4 shows one merely illustrative iontophoresis system (200). Iontophoresis system (200) of this example comprises an earplug (220), fluid source (140), control unit (170), and ground pad (180). Earplug (220) is configured to be inserted into a patient's ear and remain there without needing a separate component like a headframe to hold it in place. By way of example only, a biocompatible adhesive may be used to assist in holding earplug (220) in place within a patient's ear canal. Earplug (220) includes a pair of gripping features (222) that are configured to be gripped and thereby serve as a handle during insertion of earplug (220) in a patient's ear. Earplug (220) also includes a pull-tab (228) that may be gripped and pulled to assist in removing earplug (220) from the patient's ear. Of course, these features are mere examples, and any other suitable kinds of gripping features may be incorporated into earplug (220). While only one earplug (220) is shown, it should be understood that iontophoresis system (200) may have two earplugs (220) that may be used simultaneously.

Figure 5:
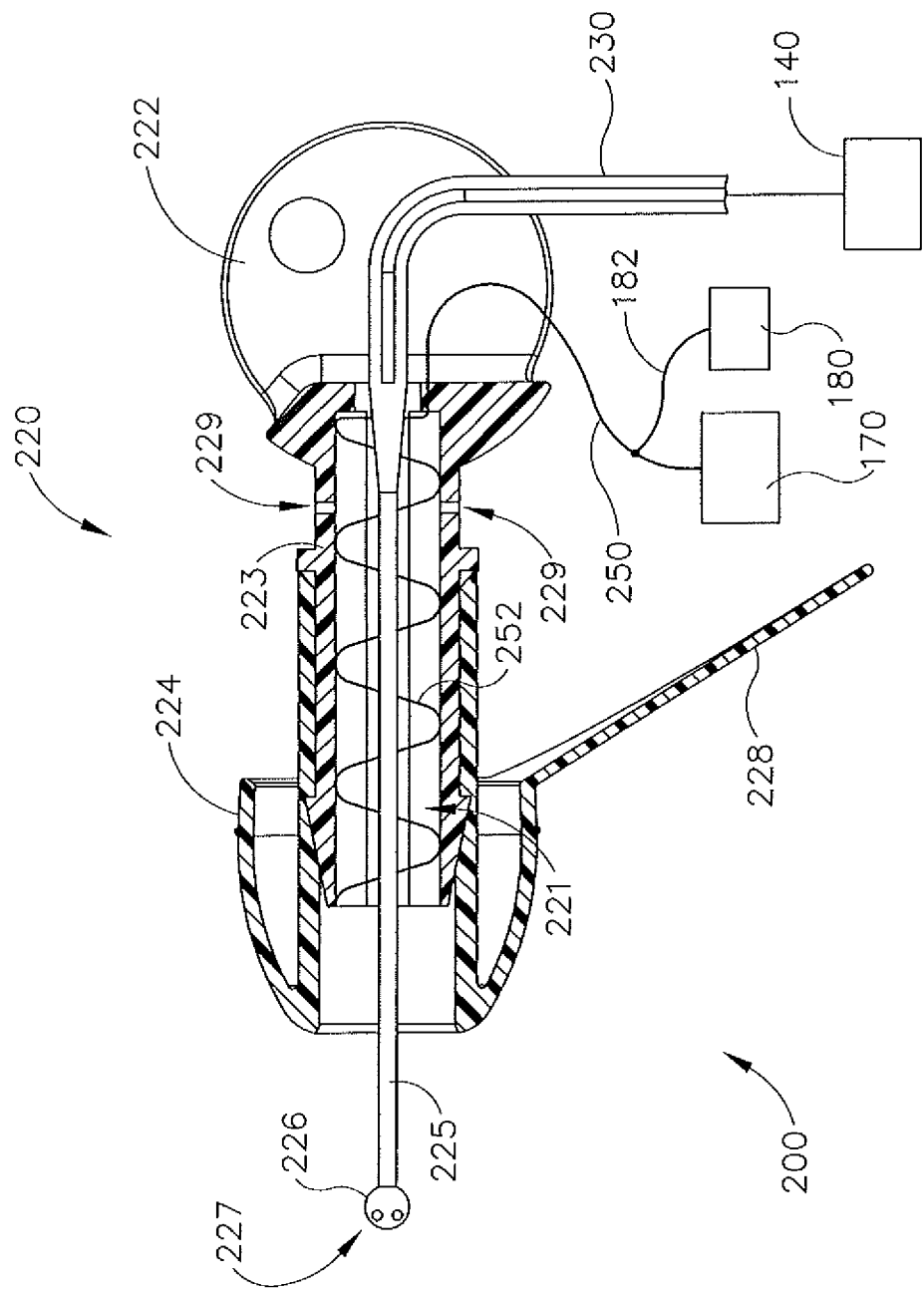
FIG. 5 depicts a cross-sectional side view of the earplug of FIG. 4.

In some versions, earplug (220) is configured and operable in accordance with at least some of the teachings of U.S. Pub. No. 2014/0102461, entitled "Adhesive Earplugs Useful for Sealing the Ear Canal," published Apr. 17, 2014, the disclosure of which is incorporated by reference herein. As best seen in FIG. 5, earplug (220) of the present example includes a flexible sealing element (224) and a distally projecting nozzle (226). Sealing element (224) is configured to provide a fluid tight seal against the patient's ear canal when earplug (220) is inserted in the patient's ear canal. In some instances, and as noted above, a biocompatible pressure sensitive adhesive is applied to the outer surface of sealing element (224) to promote a fluid tight seal against the patient's ear canal. Nozzle (226) is positioned to project into the patient's ear canal when earplug (220) is inserted in the patient's ear canal, such that nozzle (226) is spaced lateral to the tympanic membrane (TM). Nozzle (226) has spray apertures (227) and is secured to the distal end of a semi-rigid post (225). Post (225) provides a path for fluid communication from conduit (230) to spray apertures (227). Spray apertures (227) are thus in fluid communication with fluid source (140) via post (225) and conduit (230).

Sealing element (224) is secured to a rigid frame (223), which defines gripping features (222). Sealing element (224) and frame (223) also together define a working channel (221). Frame (223) defines a plurality of vent paths (229) in fluid communication with working channel (221). Vent paths (229) are configured to allow air to escape working channel (221) while working channel (221) fills with iontophoresis solution; yet are further configured prevent iontophoresis solution from escaping working channel (221) via vent paths (229) once working channel (221) is filled with iontophoresis solution. An iontophoresis electrode (252) in the form of a coil extends along at least part of the length of working channel (221). It should be understood that iontophoresis electrode (252) may have any other suitable configuration. Iontophoresis electrode (252) is coupled with control unit (170) via a cable (250) and is thereby operable to be activated with a positive voltage as described above. Thus, control unit (170) may activate iontophoresis electrode (252) to provide an electrorepulsive force to the iontophoresis solution ions delivered through apertures (227), to drive the anesthetic of the iontophoresis solution ions into the tympanic membrane (TM) for anesthetization of the tympanic membrane (TM) as described above.

It should be understood that the above described iontophoresis system (200) may be varied in numerous ways. Several examples of how iontophoresis system (200) may be varied will be described in greater detail below, while still other examples will be apparent to those of ordinary skill in the art in view of the teachings herein. While the various iontophoresis systems described herein have been mentioned in relation to PETDD (10) and PE tube (20) delivery, it should be understood that any of the iontophoresis systems described herein may be used before a manual delivery of a PE tube (20), such that the iontophoresis systems described herein do not necessarily need to be used in conjunction with a PETDD (10). It should also be understood that iontophoresis systems may be used in various other clinical contexts, such that the iontophoresis systems described herein do not necessarily need to be used in the context of a PE tube (20) delivery or in other procedures in a patient's ear. The teachings herein may be readily applied to iontophoresis systems that are used in various other procedures and in various other parts of the human anatomy. Alternative systems and settings in which the teachings herein may be applied will be apparent to those of ordinary skill in the art.

III. EXEMPLARY FLUID FLOW VARIATIONS FOR IONTOPHORESIS SYSTEM

As noted above, vent paths (229) of earplug (220) are configured to allow air to escape working channel (221) while working channel (221) and the patient's ear canal fills with iontophoresis solution. In some instances, it may be desirable to relocate and/or modify the structure associated with vent paths (229). In particular, there may be instances during use of earplug (220) where iontophoresis solution escapes through vent paths (229) and leaves a proximal portion of iontophoresis electrode (252) exposed to air. For instance, if the patient talks, coughs, swallows, cries, yawns, or otherwise moves their lower jaw, the motion associated with such activity may cause variation in the effective volume of the patient's ear canal. This variation of the effective volume of the patient's ear canal may in turn drive at least some iontophoresis solution through vent paths (229). The resulting exposure of even just a portion of iontophoresis electrode (252) to air may adversely affect the iontophoretic performance of earplug (220). In instances where the entire iontophoresis electrode (252) is left exposed to air, the iontophoresis procedure may be completely interrupted until the physician injects more iontophoresis solution into earplug (220).

It may therefore be desirable to relocate and/or modify the structure associated with vent paths (229) in order to provide greater tolerance to variations in the effective volume of the patient's ear canal, to thereby reduce the risk of even a portion of iontophoresis electrode (252) being exposed to air during an iontophoresis procedure. The following example includes a variation of earplug (220) where the vent path is relocated. However, it should be understood that the following example is merely illustrative. Other suitable variations will be apparent to those of ordinary skill in the art in view of the teachings herein.

Figure 6:
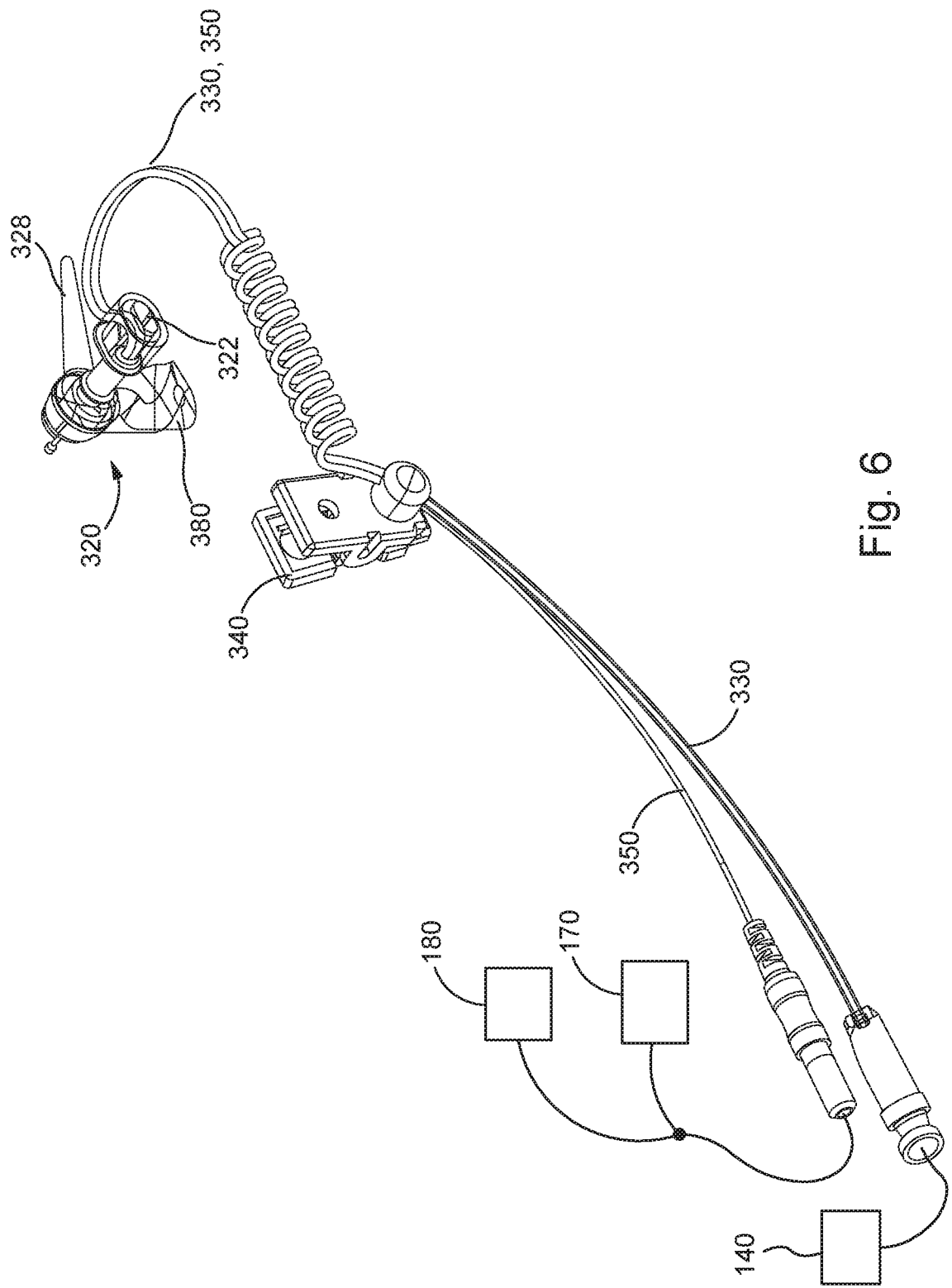
FIG. 6 depicts a perspective view of another exemplary iontophoresis system incorporating an earplug.

FIG. 6 depicts another exemplary iontophoresis system (300) that may be used to anesthetize a patient's tympanic membrane (TM), such as before a inserting a PE tube (20) into the tympanic membrane (TM) as described above. Iontophoresis system (300) of this example is substantially similar to iontophoresis system (200) described above, except where otherwise noted herein. Iontophoresis system (300) comprises an earplug (320), which is substantially similar to earplug (220) described above, except earplug (320) is generally configured to provide improved management of fluid flow in response to volumetric changes in a patient's ear during an iontophoresis procedure. Like with earplug (220), earplug (320) is in communication with fluid source (140) via a conduit (330) that is in the form of flexible tubing. Also like with earplug (220), earplug (320) is in communication with control unit (170) and ground pad (180) via a cable (350). Conduit (330) and cable (350) are coupled together along a shared length extending between a clip (340) and earplug (320). Clip (340) is operable to selectively secure the combination of conduit (330) and cable (350) to the patient's clothing and/or to any other suitable structure.

Earplug (320) is configured to be inserted into a patient's ear and remain there without needing a separate component like a headframe to hold it in place. As will be described in greater detail below, a biocompatible pressure sensitive adhesive is be used to assist in holding earplug (320) in place within a patient's ear canal. Earplug (320) includes a gripping feature (322) that is configured to be gripped and thereby serve as a handle during insertion of earplug (320) in a patient's ear. Earplug (320) also includes a pull-tab (328) that may be gripped and pulled to assist in removing earplug (320) from the patient's ear. Of course, these features are merely illustrative examples, and any other suitable kinds of gripping features may be incorporated into earplug (320). While only one earplug (320) is shown, it should be understood that iontophoresis system (300) may have two earplugs (320) that may be used in both of the patient's ears simultaneously or in a sequence.

Figure 7:
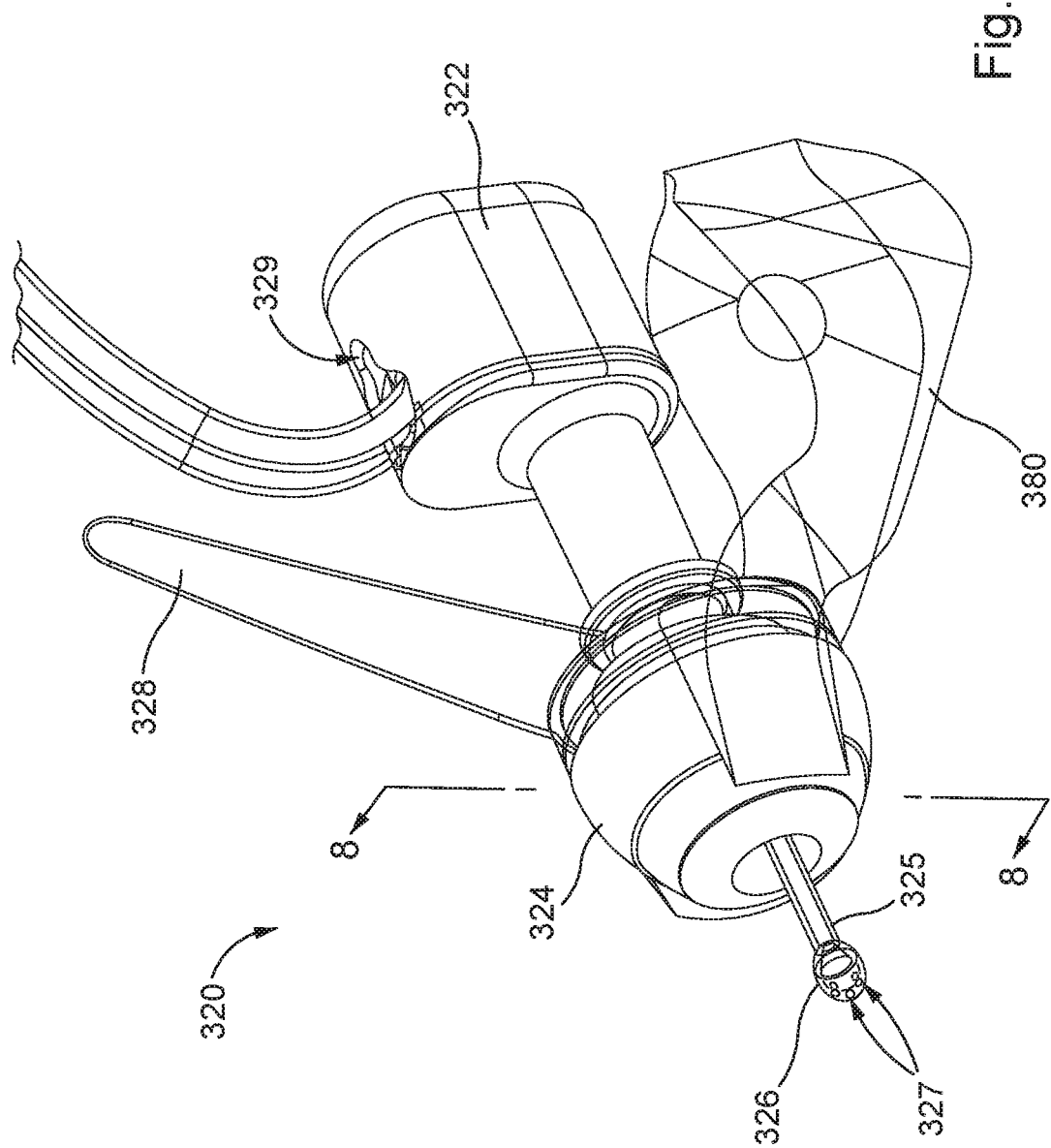
FIG. 7 depicts a perspective view of the earplug of FIG. 6.
Figure 8:
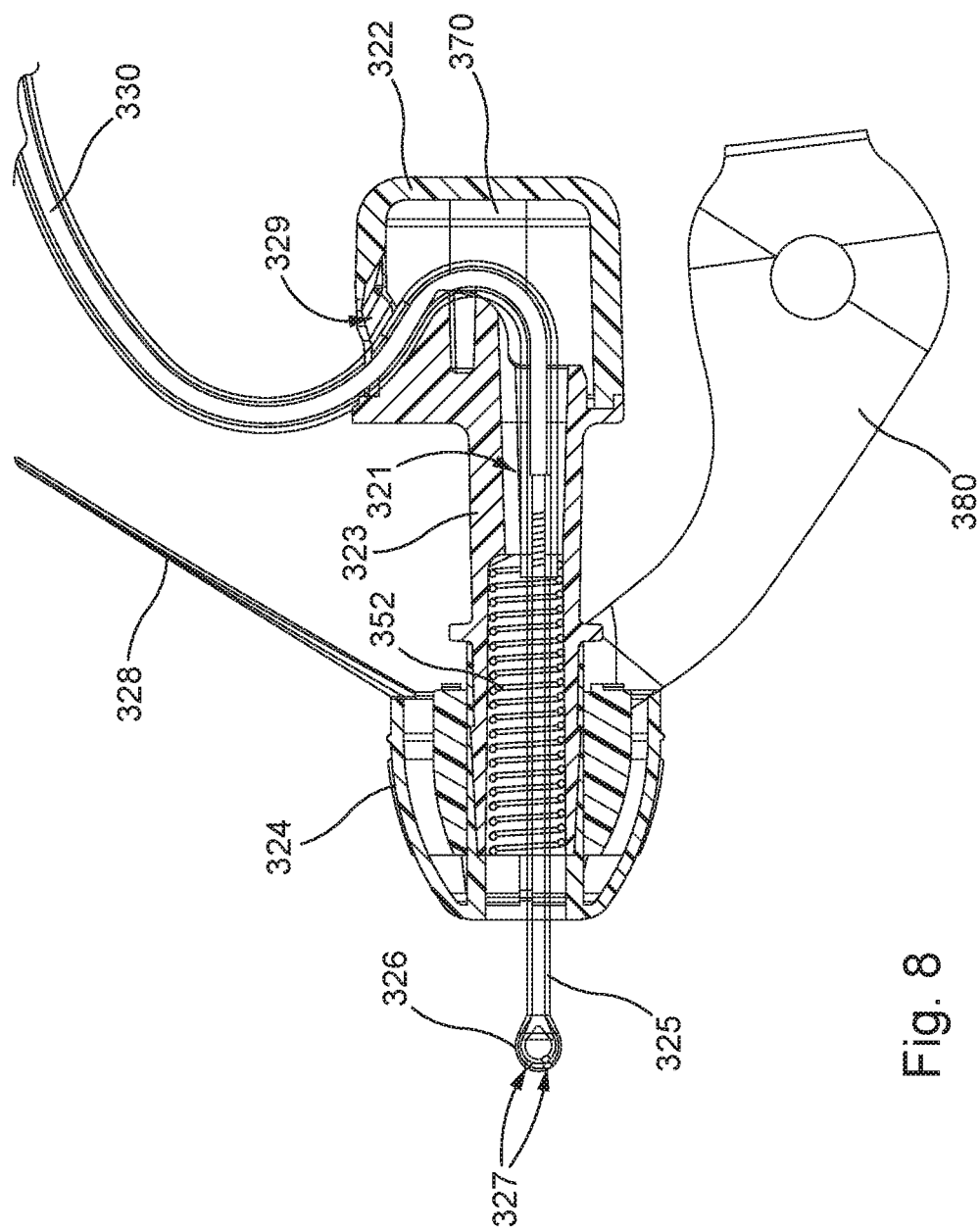
FIG. 8 depicts a side cross-sectional view of the earplug of FIG. 6, with the cross-section taken along line 8-8 of FIG. 7.

As best seen in FIGS. 7-8, earplug (320) of the present example includes a flexible sealing element (324) and a distally projecting nozzle (326). Sealing element (324) is configured to provide a fluid tight seal against the patient's ear canal when earplug (320) is inserted in the patient's ear canal. In the present example, a pressure sensitive adhesive is applied to the outer surface of sealing element (324) to promote a fluid tight seal against the patient's ear canal. Nozzle (326) is positioned to project into the patient's ear canal when earplug (320) is inserted in the patient's ear canal, such that nozzle (326) is spaced lateral to the tympanic membrane (TM). Nozzle (326) has a plurality of spray apertures (327) and is secured to the distal end of a semi-rigid post (325). Post (325) defines a lumen providing a path for communication of fluid from conduit (330) to spray apertures (327). Spray apertures (327) are thus in fluid communication with fluid source (140) via post (325) and conduit (330). Sealing element (324) is secured to a rigid frame (323). Sealing element (324) and frame (323) together define a working channel (321), as will be described in greater detail below.

Gripping feature (322) is fixedly secured to rigid frame (323). Gripping feature (322) and frame (323) cooperate to define a reservoir (370). Reservoir (370) is in fluid communication with working channel (321). Reservoir (370) extends laterally relative to a longitudinal axis defined by post (325). Thus, reservoir (370) and working channel (321) together form an L-shaped cavity. As will be described in greater detail below, this L-shaped cavity operates to maintain fluid contact with iontophoresis electrode (352) even when a patient's ear canal experiences volumetric changes throughout the iontophoresis procedure. Frame (323) also defines at least one vent path (329), which is also in fluid communication with reservoir (370). Vent path (329) is configured to allow air to escape reservoir (370) when reservoir (370) fills with iontophoresis solution, as will be described in greater detail below. In the present example, vent path (329) is formed as a circular opening with a diameter of approximately 0.025 inches. Alternatively, vent path (329) may have any other suitable size or configuration.

An iontophoresis electrode (352) in the form of a coil extends along at least part of the length of working channel (321). It should be understood that iontophoresis electrode (352) may have any other suitable configuration. Iontophoresis electrode (352) is coupled with control unit (170) via cable (350) and is thereby operable to be activated with a positive voltage as described above. Thus, control unit (170) may activate iontophoresis electrode (352) to provide an electrorepulsive force to the iontophoresis solution ions delivered through apertures (327), to drive the anesthetic of the iontophoresis solution ions into the tympanic membrane (TM) for anesthetization of the tympanic membrane (TM) as described above.

Unlike earplug (220) described above, earplug (320) of the present example is configured to tolerate volumetric changes in a patient's ear during an iontophoresis procedure without letting iontophoresis electrode (352) become exposed to air. In particular, reservoir (370) of the present example is configured to effectively increase the volume of working channel (321), thereby providing a spacing between vent path (329) and iontophoresis electrode (352) that is greater than the spacing between vent paths (229) and iontophoresis electrode (252). In the present example, reservoir (370) and working channel (321) provide a combined volume that is about three times that of working channel (221) described above. In some other examples, reservoir (370) and working channel (321) provide a combined volume that is between about two times and about four times that of working channel (221). Of course, reservoir (370) and working channel (321) may instead provide any other suitable combined volume in relation to the volume of working channel (221).

Unlike earplug (220) described above, earplug (320) of the present example is configured such that vent path (329) is repositioned for management of fluid flow in response to volumetric changes in a patient's ear canal. As can be seen, vent path (329) of the present example is positioned adjacent to reservoir (370) at the furthest lateral point of reservoir (370). As will be described in greater detail below, the above described positioning of vent path (329) directs fluid out of reservoir (370) such that any open space created by displaced fluid remains within reservoir (370). Although vent path (329) of the present example is shown as being integral with an opening for conduit (330), it should be understood that in other examples vent path (329) is a discrete opening in gripping feature (322), spaced away from the point at which conduit (330) enters gripping feature (322).

Figure 9:
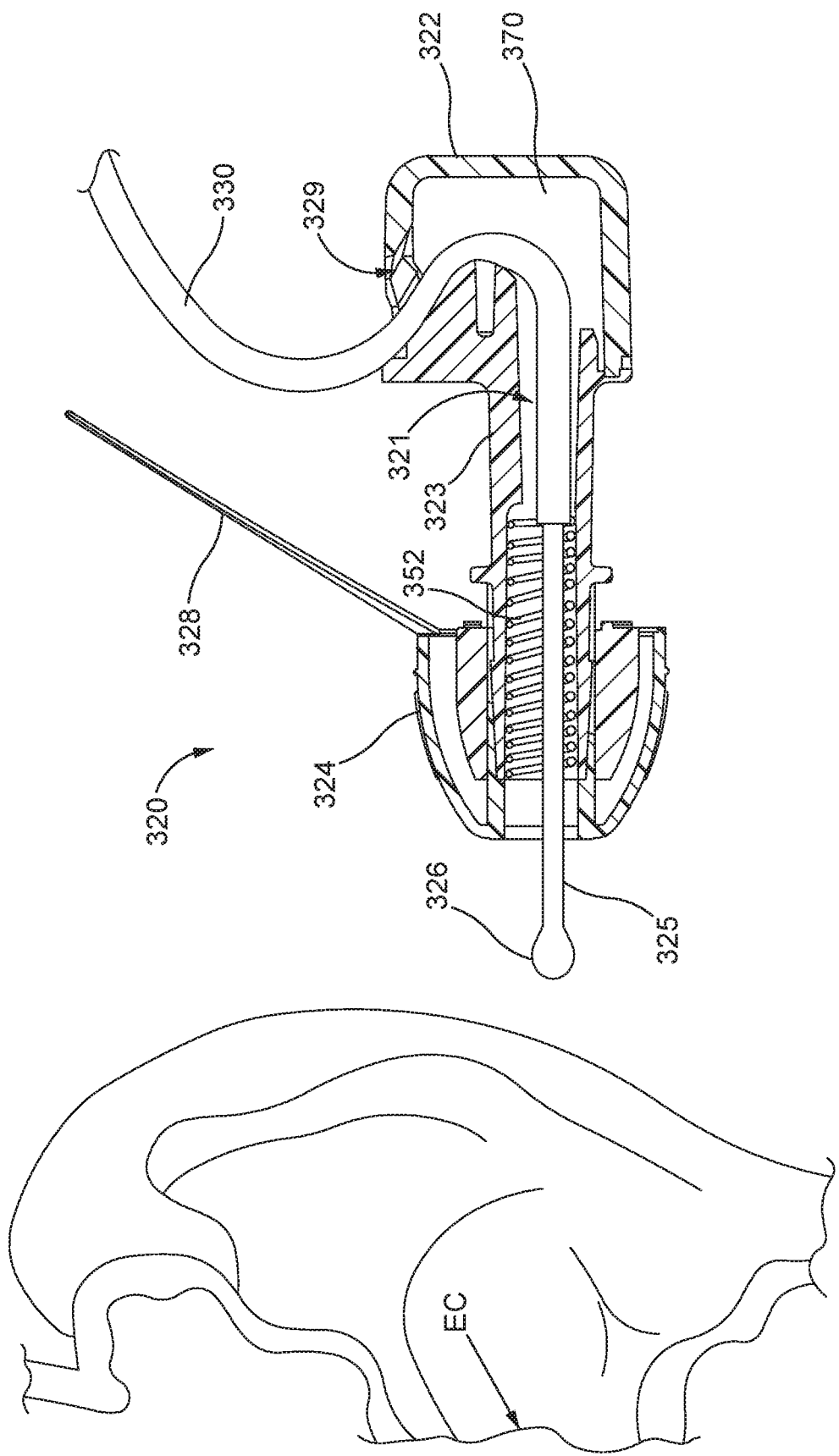
FIG. 9 depicts another side cross-sectional view of the earplug of FIG. 6, with the earplug positioned adjacent to a patient's ear at a horizontal orientation.
Figure 10:
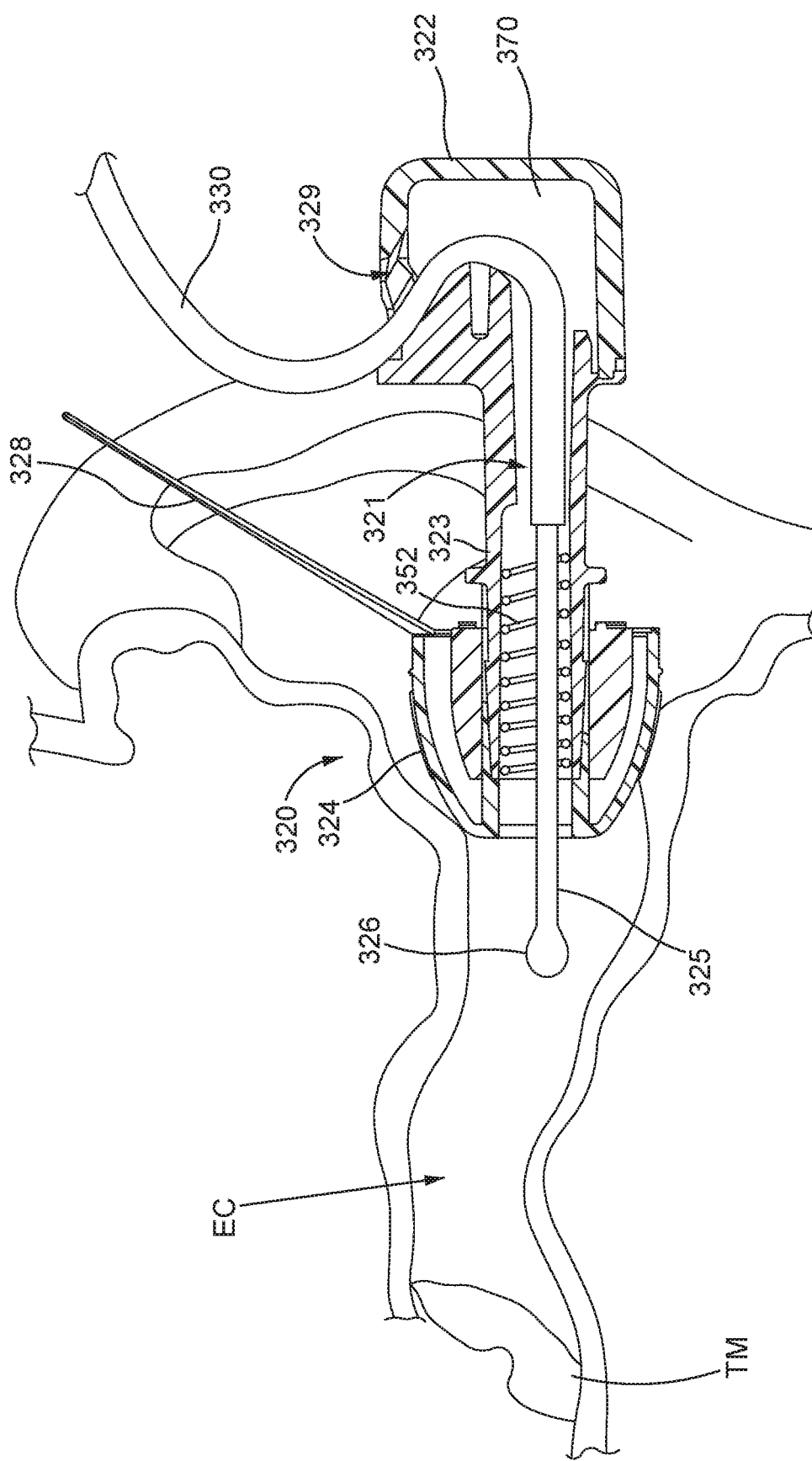
FIG. 10 depicts another side cross-sectional view of the earplug of FIG. 6, with the earplug positioned within a patient's ear canal at a horizontal orientation.

FIGS. 9-15 show a merely illustrative use of earplug (320). As can be seen in FIG. 9, earplug (320) is initially positioned outside of a patient's ear. At this stage, fluid has not yet been injected into earplug (320). The operator may begin the iontophoresis procedure by inserting sealing element (324) of earplug (320) into a patient's ear canal (EC). As can be seen in FIG. 10, sealing element (324) is positioned to bear against the walls of the ear canal (EC), simultaneously securing earplug (320) and creating a fluid seal between sealing element (324) and the wall of the ear canal (EC). The sealing of the ear canal (EC) creates a fluid tight cavity between tympanic membrane (TM) and earplug (320) that may be used to contain iontophoresis fluid. While not shown in FIGS. 9-10, a liner strip (380) as described below may be used to assist the operator in positioning earplug (320) in the ear canal (EC) without the operator's fingers getting stuck to the pressure sensitive adhesive on sealing element (324).

Figure 11:
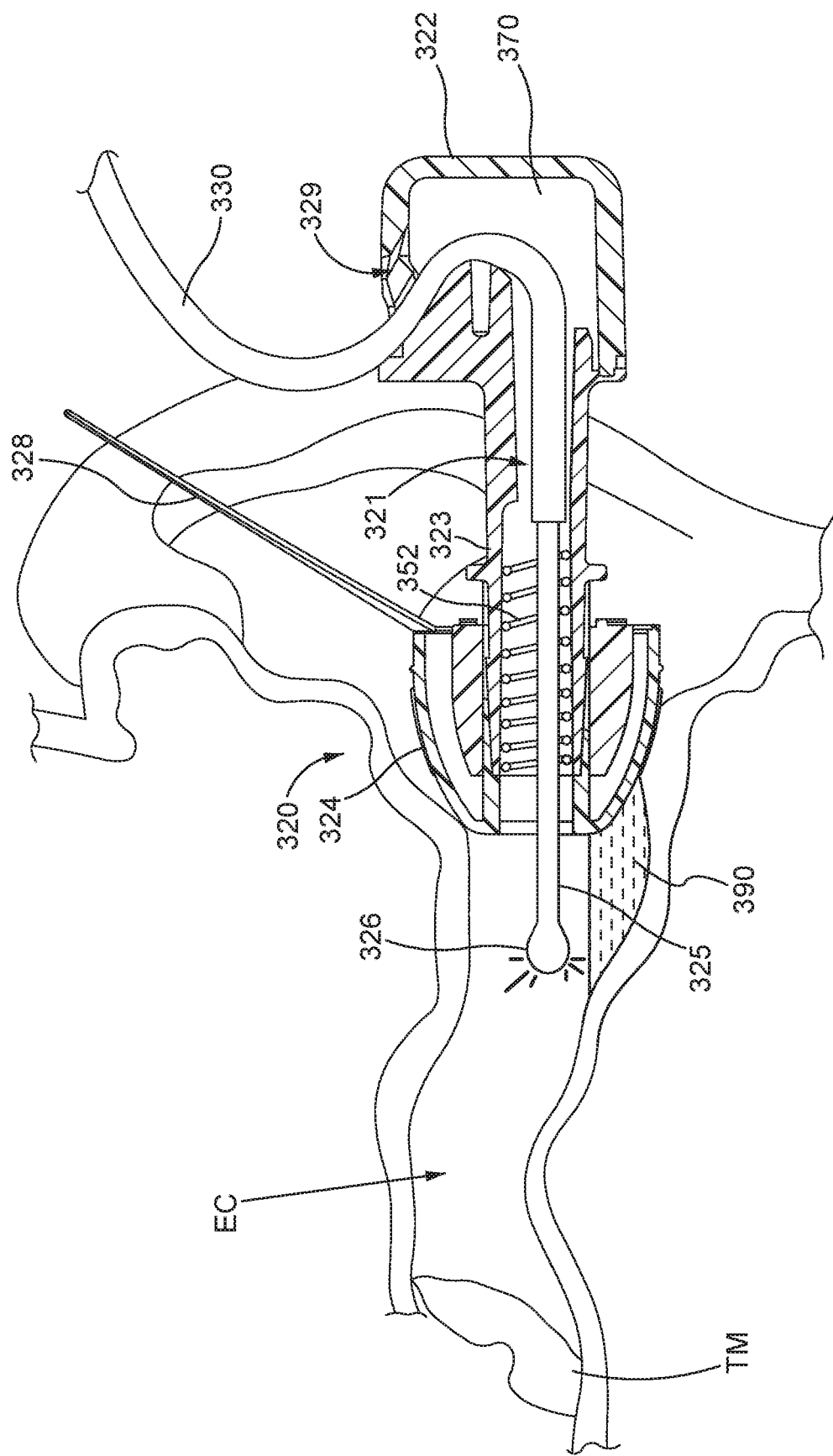
FIG. 11 depicts another side cross-sectional view of the earplug of FIG. 6, with the earplug positioned within a patient's ear canal at a horizontal orientation, and with the earplug filling a patient's ear canal with iontophoresis fluid.
Figure 12:
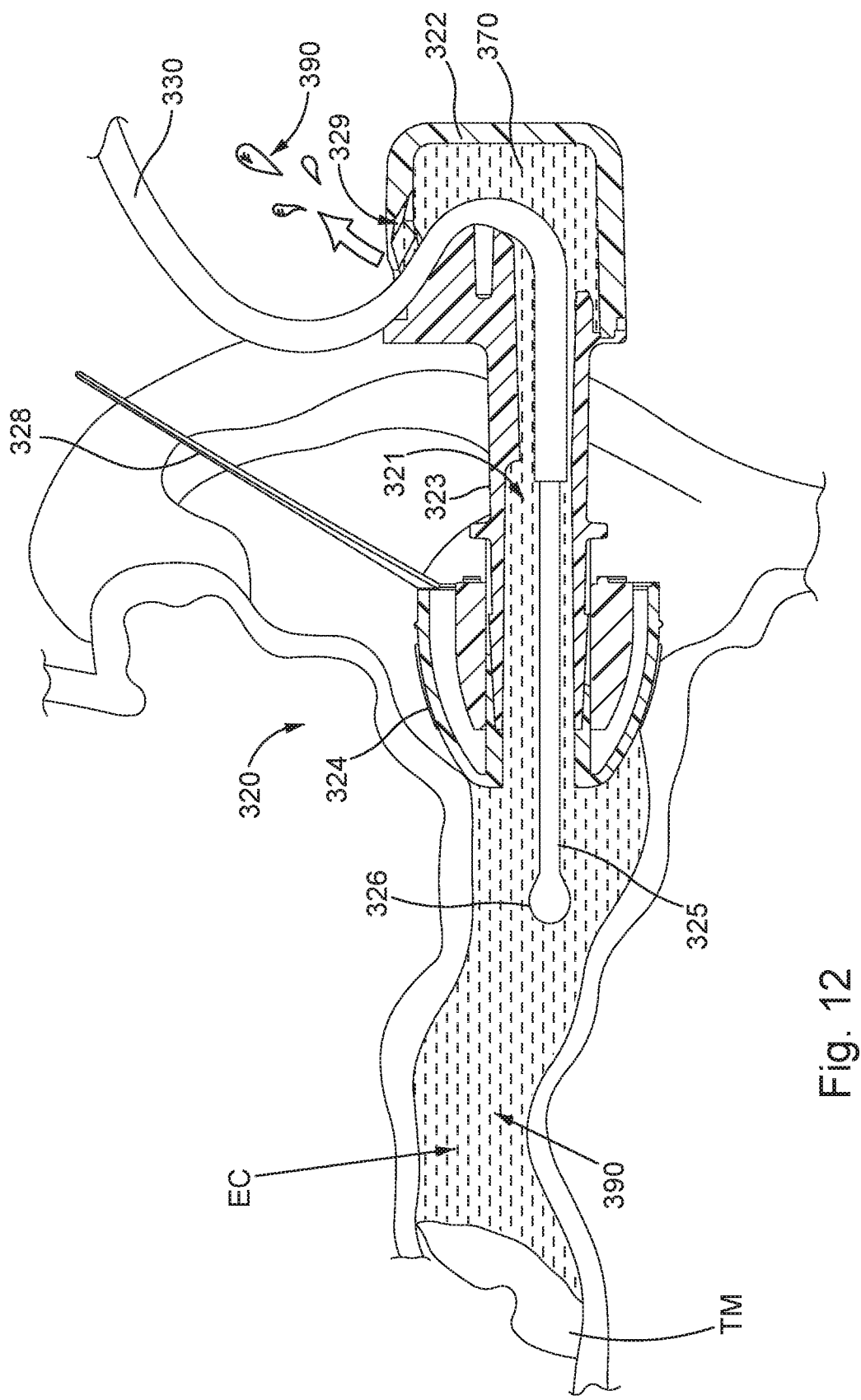
FIG. 12 depicts another side cross-sectional view of the earplug of FIG. 6, with the earplug positioned within a patient's ear canal at a horizontal orientation, and with a patient's ear canal fully filled with iontophoresis fluid and excess fluid escaping through a vent path of the earplug.

Once earplug (320) is secured in the patient's ear canal (EC), the operator may begin administration of iontophoresis fluid (390) to the ear canal (EC) via conduit (330) and nozzle (326), as can be seen in FIG. 11. As fluid (390) is administered, the ear canal (EC), working channel (321) and reservoir (370) will fill with fluid (390); and the air displaced from the ear canal (EC), working channel (321) and reservoir (370) will flow out to the atmosphere through vent path (329). The operator may continue administering fluid (390) until fluid (390) is observed flowing out through vent path (329) as shown in FIG. 12. Once fluid flows through vent path (329), the ear canal (EC), working channel (321), reservoir (370) are full of fluid (390) and earplug (320) is ready to activate iontophoresis electrode (352) to thereby provide an electrorepulsive force to the iontophoresis fluid ions. In some versions, gripping feature (322) is transparent, enabling the operator to visually observe reservoir (370) filling with fluid (390). This may enable the operator to be more ready to cease injecting fluid (390) via conduit (330) when the level of fluid (390) reaches vent path (329).

Figure 13:
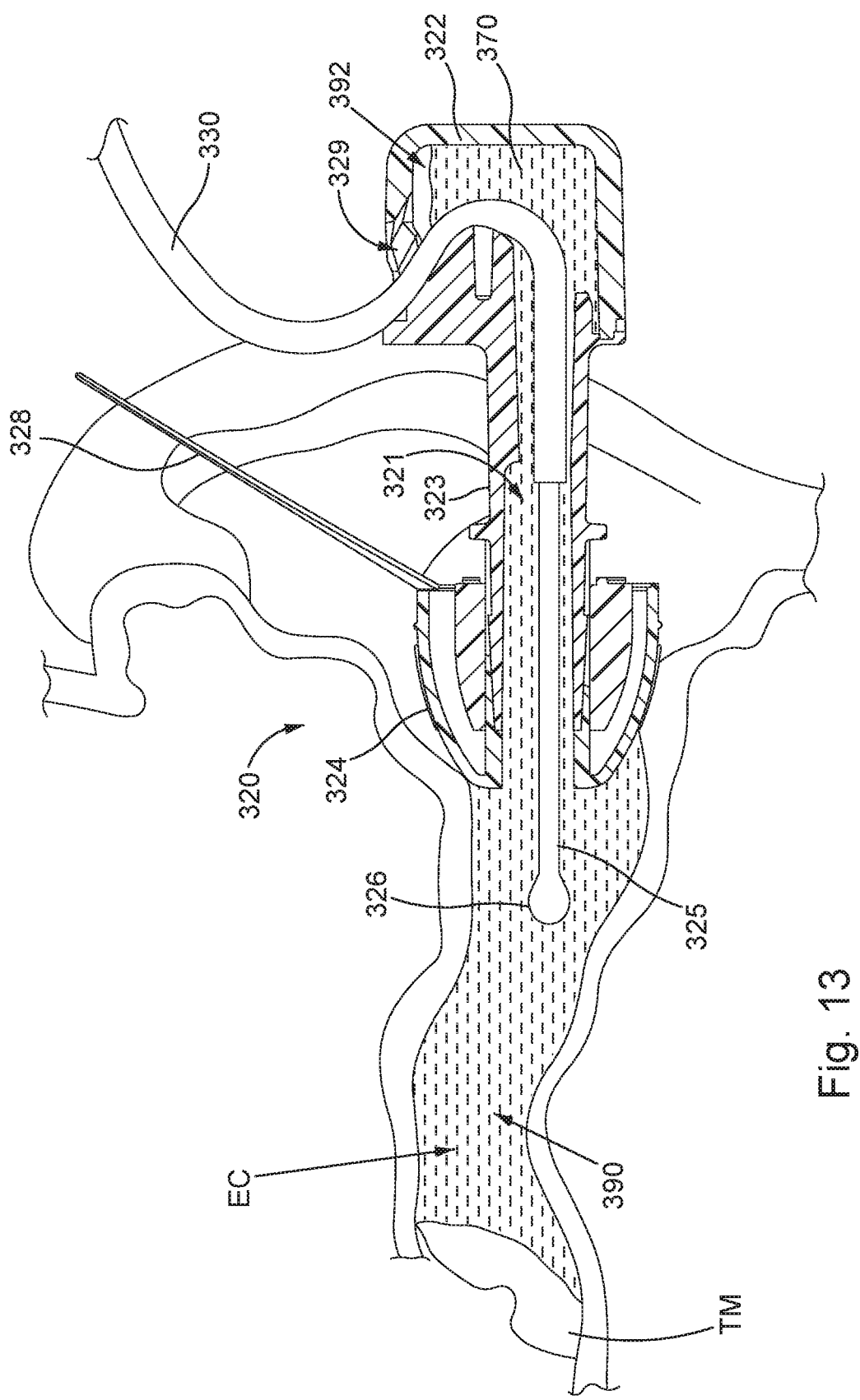
FIG. 13 depicts another side cross-sectional view of the earplug of FIG. 6, with the earplug positioned within a patient's ear canal at a horizontal orientation, and with the earplug in a state ready for activation of an electrode of the earplug.

Prior to activation of electrode (352), the operator may remove a fluid delivery device (not shown) such as a syringe from conduit (330). It should be understood that in some circumstances removal of such a device may result in some loss of fluid (390) from working channel (321). By way of example only, in some examples this may result in a loss of about 0.04 cc of fluid (390). As a result, an air pocket (392) of a corresponding volume may form adjacent to vent path (329) in reservoir (370), as shown in FIG. 13. It should be understood that this air pocket (392) is substantially spaced away from iontophoresis electrode (352), such that iontophoresis electrode (352) remains fully submerged in fluid (390) with no meaningful risk of any portion of electrode (352) being exposed to air.

Figure 14:
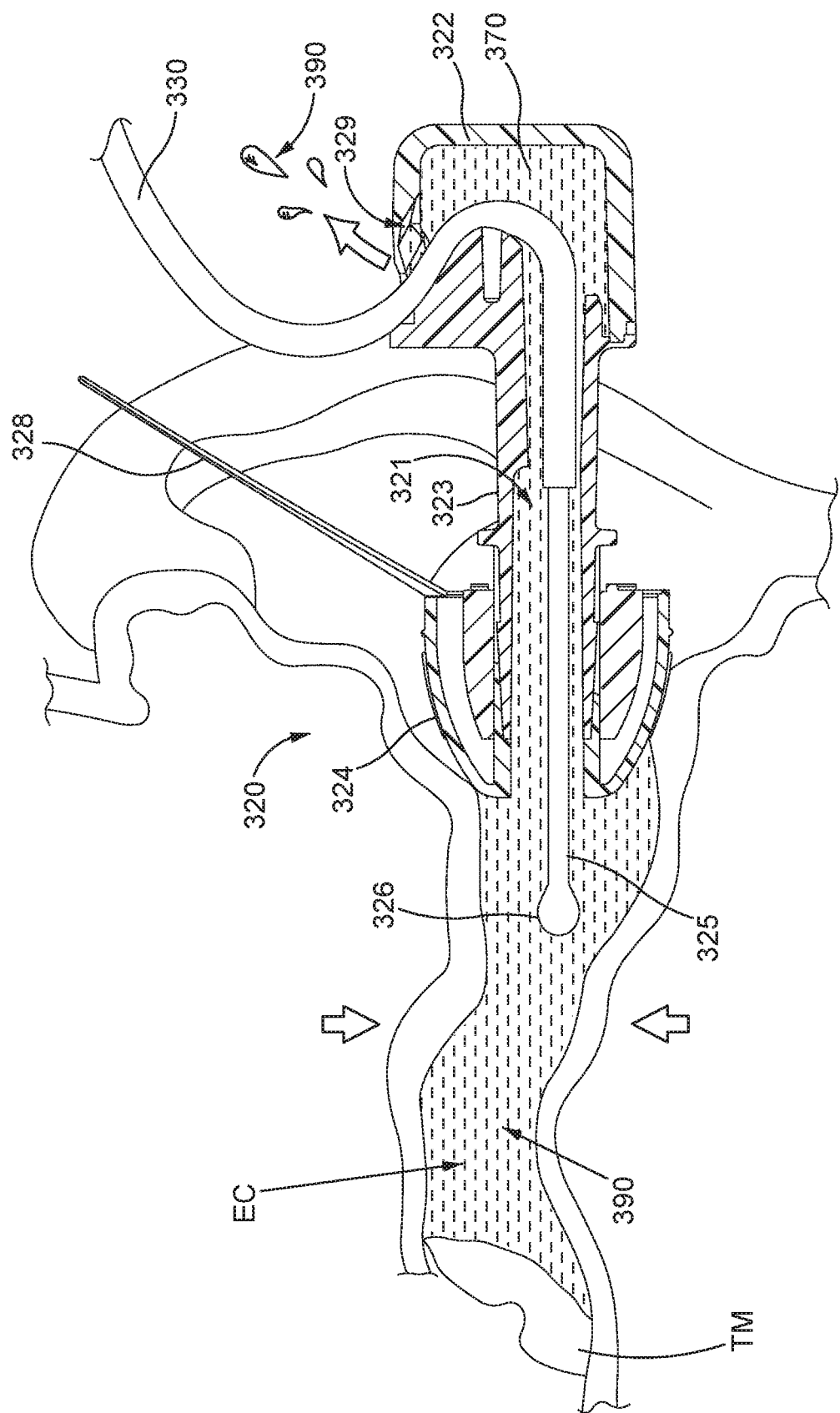
FIG. 14 depicts another side cross-sectional view of the earplug of FIG. 6, with the earplug positioned within a patient's ear canal at a horizontal orientation, and with the patient's ear canal exhibiting volumetric changes, thereby expelling iontophoresis fluid through the vent path.
Figure 15:
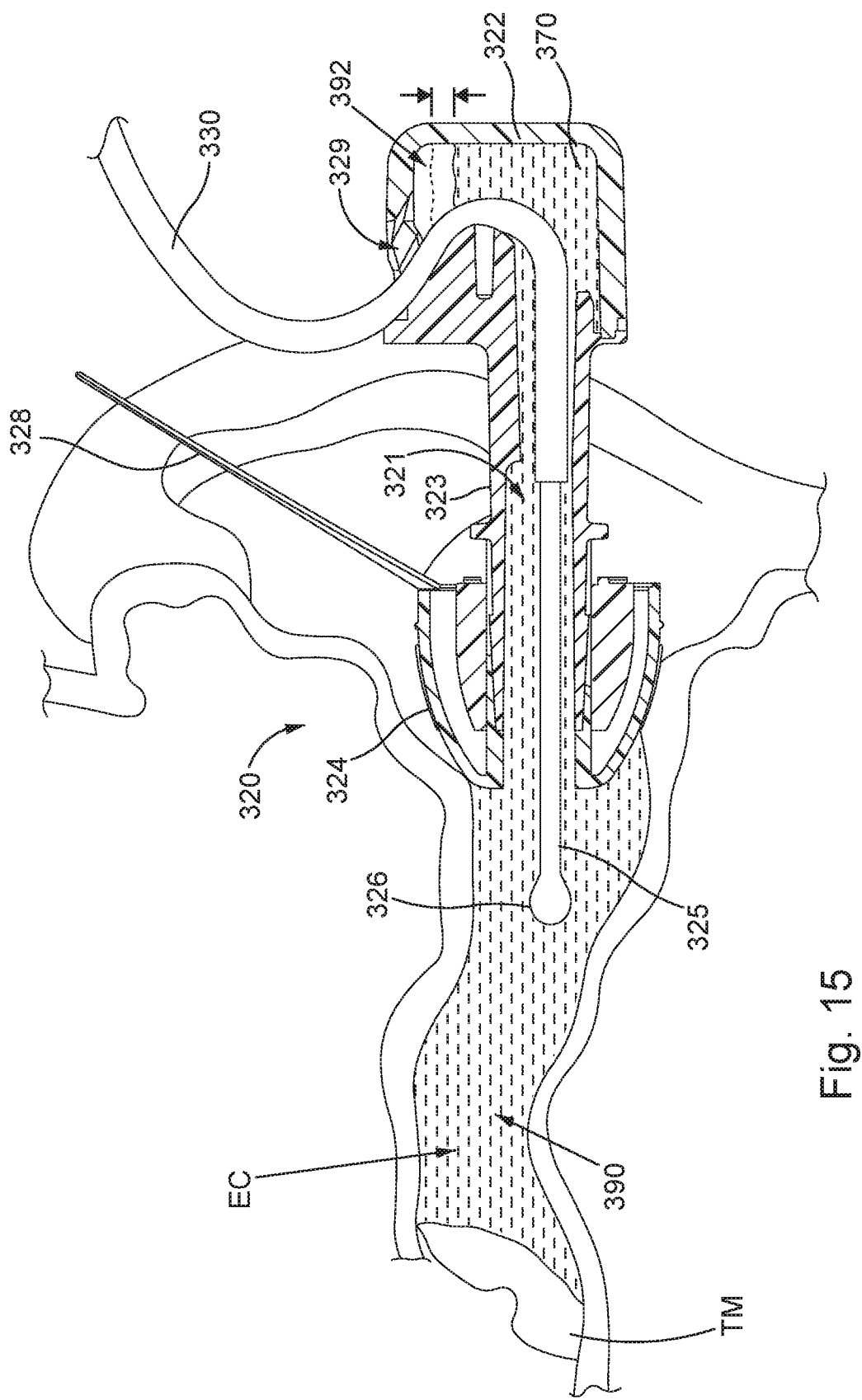
FIG. 15 depicts another side cross-sectional view of the earplug of FIG. 6, with the earplug positioned within a patient's ear canal at a horizontal orientation, and with at least some fluid expelled from a reservoir of the earplug.

During the iontophoresis procedure, the patient may talk, cough, swallow, cry, yawn, or otherwise move their lower jaw, and the motion associated with such activity may cause variation in the effective volume of the patient's ear canal (EC). Such volumetric changes may cause a pumping action, which will vary the level of fluid (390) in reservoir (370). In some instances, this variation of the level of fluid (390) may displace fluid (390) out of vent path (329), as shown in FIG. 14. As fluid (390) is displaced out of vent path (329) the volume of fluid (390) disposed in the ear canal (EC), working channel (321), reservoir (370) is reduced by a corresponding amount. As can be seen in FIG. 15, such a reduction in fluid (390) will correspondingly cause the air pocket (392) in reservoir (370) to expand and contract. Even with further volumetric changes in the patient's ear canal (EC), the air pocket (392) may eventually reach a point where fluid (390) stops leaking from vent path (329) and the size of air pocket (392) simply expands and contracts in response to the volumetric changes in the patient's ear canal (EC). Because of the volume and L-shape provided by reservoir (370), the air pocket (392) will remain positioned exclusively in reservoir (370) instead of extending to the remainder of working channel (321) or the ear canal (EC). Thus, reservoir (370) maintains complete contact between fluid (390) and electrode (352), preventing exposure of electrode (352) to air, thereby maintaining full electrical conductivity between fluid (390) and electrode (352).

Figure 16:
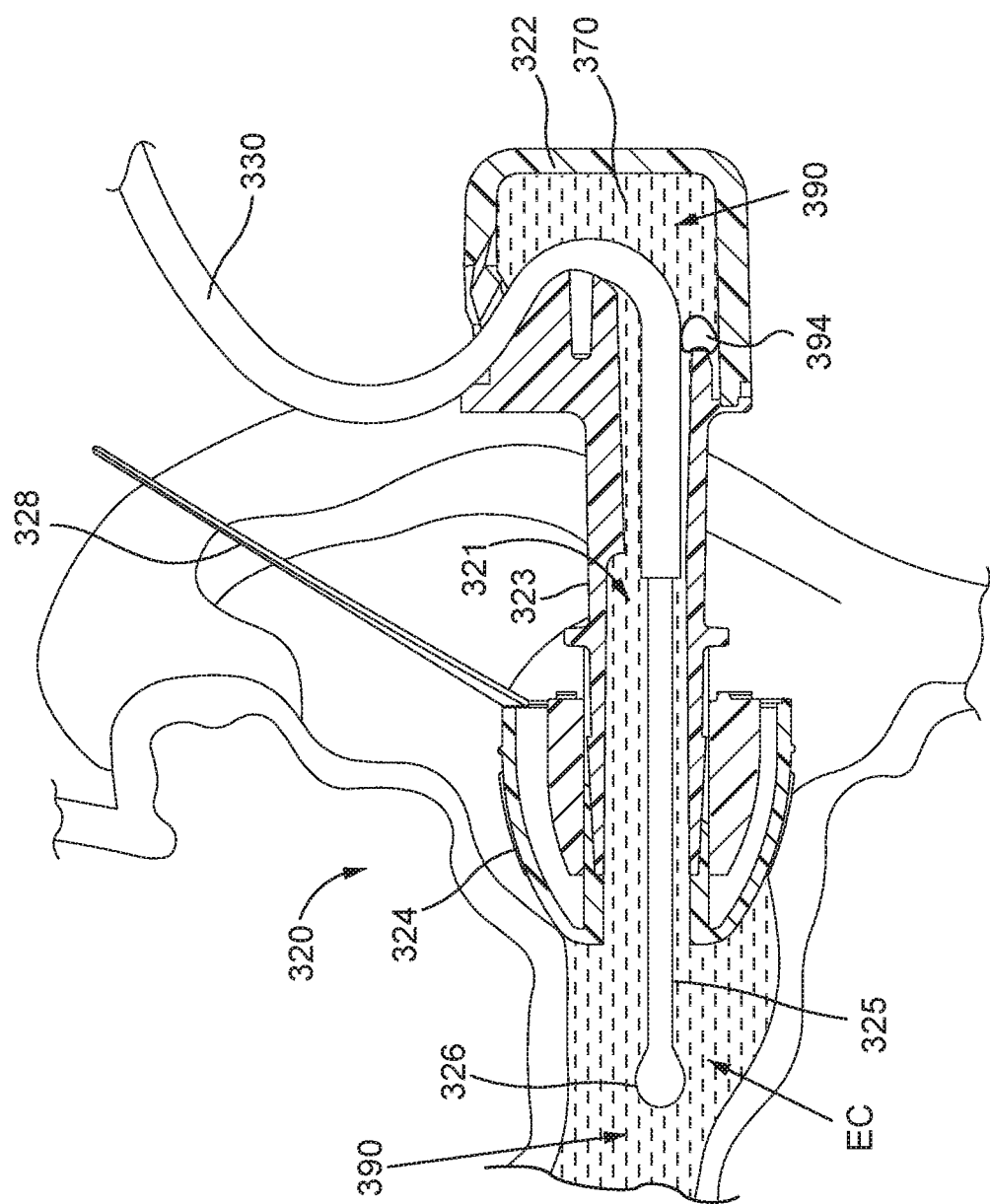
FIG. 16 depicts yet another side cross-sectional view of the earplug of FIG. 6 with the earplug positioned within a patient's ear canal at a vertical orientation.

In some instances earplug (320) may be used in an inverted position (i.e., at a vertical orientation). In particular, the operator may wish to insert earplug (320) in a patient's ear while the patient's head is oriented toward the ground. During such an operation, reservoir (370) and vent path (329) may generally provide the same function as described above but with different positioning of the air in reservoir (370). As can be seen in FIG. 16, with earplug (320) positioned vertically, an air bubble (394) is disposed within reservoir (370) away from vent path (329). Surface tension at the interface between the air bubble (394) and the fluid (390) keeps the air bubble (394) within reservoir (370) and away from the rest of working channel (321). Similarly, surface tension between fluid (390) and vent path (329) maintains fluid (390) within reservoir (370), while permitting some fluid (390) to be released in response to volumetric changes in the ear canal (EC). It should be understood that to maintain the air bubble (394) in the position shown the interface between reservoir (370) and the remainder of working channel (321) is sized to correspond to the size of the air bubble (394). Additionally, the extension of post (325) though working channel (321) further reduces the size of working channel (321) to further prevent any travel of the air bubble (394).

IV. EXEMPLARY LINER STRIP FOR USE WITH EARPLUG

As noted above, a pressure sensitive adhesive may be provided on sealing element (324) in order to provide a more secure and fluid tight fit between sealing element (324) and the wall of the patient's ear canal (EC). It may be desirable to provide a feature that facilitates gripping and positioning of earplug (320) without the operator's fingers getting stuck to the pressure sensitive adhesive on sealing element (324). To that end, earplug (320) of the present example includes a liner strip (380).

Figure 17:
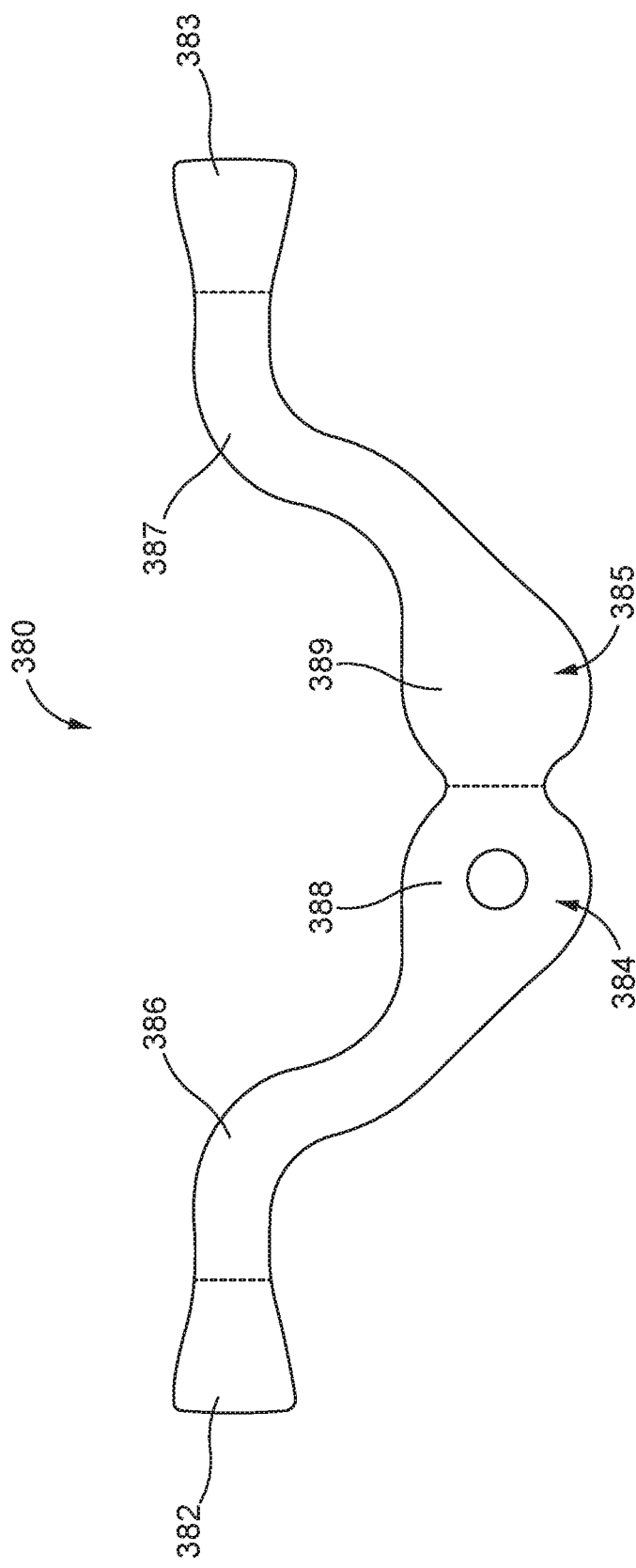
FIG. 17 depicts a front elevational view of a liner strip that may be used with the earplug of FIG. 6, with the liner strip in a flat and unfolded configuration.
Figure 18:
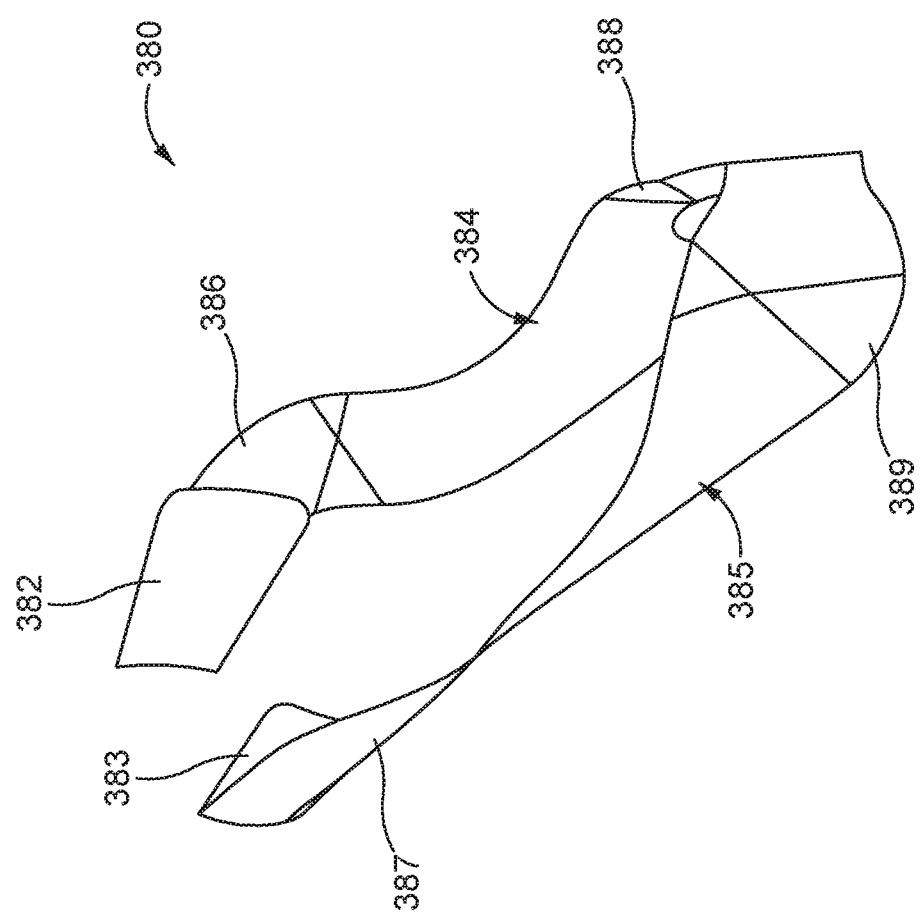
FIG. 18 depicts a perspective view of the liner strip of FIG. 17 in a folded configuration.
Figure 19:
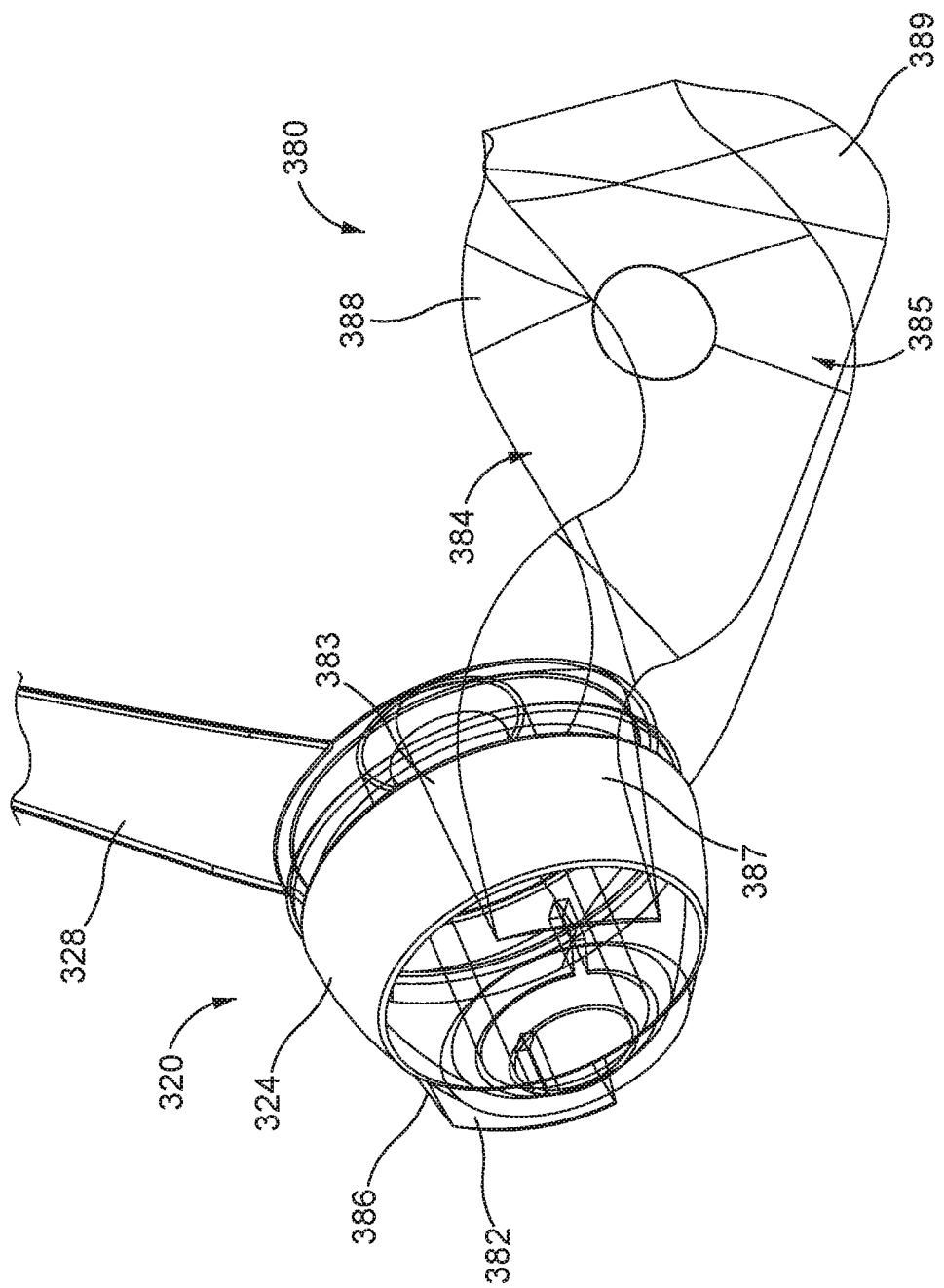
FIG. 19 depicts detailed perspective view of the liner strip of FIG. 17 attached to the earplug of FIG. 6 in the folded configuration of FIG. 18.

FIGS. 17-19 show liner strip (380) in greater detail. As can be seen, liner strip (380) of the present example is constructed as a single generally flat part having a shape generally resembling an imperial moustache, or (when turned 180° from the view in FIG. 17) a handlebar mustache. At least a portion of liner strip (380) is coated with fluorosilicone, providing a low-tack release surface that facilitates peeling of liner strip (380) away from the pressure sensitive adhesive on sealing element (324). Liner strip (380) itself comprises a generally flexible 0.0009 inch thick polyethylene terephthalate (PET) film. Alternatively, liner strip (380) may comprise a variety of other suitable materials having a range of thicknesses.

The shape of liner strip (380) divides liner strip (380) into four discrete portions (382, 383, 384, 385). In particular, liner strip (380) may be folded along three fold lines (shown in broken lines in FIG. 17) to more readily define each portion (382, 383, 384, 385). When folded, liner strip (380) defines two attachment portions (382, 383) and two gripping portions (384, 385). As can best be seen in FIG. 18, attachment portions (382, 383) are folded in a reverse direction to define a surface suitable for attachment of liner strip (380) to opposing sides of sealing element (324). In the present example, each attachment portion (382, 383) is also heat formed to define a slight curvature in each attachment portion (382, 383). The curvature of each attachment portion (382, 383) is entirely optional and may be omitted in some examples. However, where used, the curvature of attachment portions (382, 383) corresponds to the curvature of flexible sealing element (324) of earplug (320) to promote full apposition between attachment portions (382, 383) and sealing element (324).

As seen in FIGS. 18 and 19, each gripping portion (384, 385) extends proximally away from each respective attachment portion (382, 383). In particular, each gripping portion comprises a corresponding thin portion (386, 387) and thick portion (388, 389). Each thin portion (386, 387) curves laterally away from each attachment portion (382, 383) to orient each respective thick portion (388, 389) away from earplug (320). This feature permits thick portions (388, 389) to be used for grasping by a user to manipulate earplug (320) by grasping liner strip (380).

As can be seen in FIG. 19, liner strip (380) is placed on earplug (320) such that attachment portions (382, 383) are positioned about sealing element (324) at angular locations corresponding to the posterior and anterior walls of a patient's ear canal (EC). In some instances, this positioning corresponds to the areas of flexible sealing element (324) that will encounter the most resistance from a patient's ear canal (EC) during insertion of earplug (320). Such positioning may be desirable to ensure that the pressure sensitive adhesive on sealing element (324) fully engages the superior and inferior walls of the patient's ear canal (EC) before the pressure sensitive adhesive on sealing element (324) contacts the posterior and anterior walls of the patient's ear canal (EC). Once earplug (320) is inserted into the ear canal (EC) far enough for sealing element (324) to fully engage the posterior and anterior walls of the patient's ear canal (EC), the operator may peel away liner strip (380) to allow the pressure sensitive adhesive on sealing element (324) to contact the posterior and anterior walls of the patient's ear canal (EC). At this stage, the pressure sensitive adhesive on sealing element (324) may contact the walls of the ear canal (EC) about the entire angular perimeter of sealing element (324). Liner strip (380) may then be disposed of.

In the present example, the pressure sensitive adhesive is provided about the entire angular perimeter of sealing element (324). Also in the present example, attachment portions (382, 383) are together sized to contact approximately 40% of the surface of sealing element (324) that is coated with pressure sensitive adhesive. Alternatively, attachment portions (382, 383) may cover any other suitable portion of the surface of sealing element (324) that is coated with pressure sensitive adhesive. It should also be understood that pressure sensitive adhesive may be provided about only a portion of the angular perimeter of sealing element (324). For instance, earplug (320) may be configured such that pressure sensitive adhesive is only provided on the zones of sealing element (324) that will contact posterior and anterior walls of the patient's ear canal (EC); but not on the zones of sealing element (324) that will contact posterior and anterior walls of the patient's ear canal (EC).

As another merely illustrative example, a lubricious material (e.g., alcohol, etc.), may be applied to the pressure sensitive adhesive on sealing element (324) to aid in insertion of sealing element (324) in the ear canal (EC); with the lubricious material being configured to evaporate or otherwise dissipate to enable the pressure sensitive adhesive to adhere to the walls of the ear canal (EC) shortly after sealing element (324) is inserted in the ear canal (EC). Still other suitable variations will be apparent to those of ordinary skill in the art in view of the teachings herein.

V. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a rigid body, wherein the rigid body defines: (i) a channel, (ii) reservoir in fluid communication with the channel, and (ii) vent path in fluid communication with the reservoir, wherein the reservoir is configured to provide spacing between the channel and the vent path; (b) a flexible sealing element, wherein the sealing element is positioned distal to the rigid body; (c) a nozzle assembly, wherein the nozzle assembly comprises: (i) a nozzle head, and (ii) a post, wherein the post extends distally through the channel of the rigid body, wherein the nozzle head projects distally from a distal end of the post; and (d) an electrode, wherein the electrode is disposed within the channel of the rigid body, wherein the reservoir extends laterally from a longitudinal axis defined by the electrode.

Example 2

The apparatus of Example 1, wherein the electrode terminates at a proximal end, wherein the proximal end of the electrode is distal to the reservoir.

Example 3

The apparatus of any one or more of Examples 1 through 2, wherein the channel and the reservoir together define an L-shape.

Example 4

The apparatus of any one or more of Examples 1 through 3, wherein the channel extends distally relative to the reservoir, wherein the vent path extends laterally relative to the reservoir.

Example 5

The apparatus of any one or more of Examples 1 through 4, wherein the sealing element is configured to bear against a wall of an ear canal to thereby define a closed volume outside of a tympanic membrane in the ear canal.

Example 6

The apparatus of Example 5, wherein the reservoir is in configured to communicate with the closed volume through the channel.

Example 7

The apparatus of Example 6, wherein the vent path is configured to release excess fluid from the reservoir in response to filling of the closed volume, the channel, and the reservoir with fluid.

Example 8

The apparatus of any one or more of Examples 6 through 7, wherein the reservoir is configured to provide an air pocket between fluid and the vent path as the closed volume, the channel, and the reservoir are filled with fluid, wherein the channel is configured to maintain submersion of the electrode in the fluid while the air pocket resides in the reservoir.

Example 9

The apparatus of any one or more of Examples 5 through 8, further comprising a fluid conduit, wherein the fluid conduit is in communication with the channel, wherein the fluid conduit is configured to fill the closed volume, the channel, and the reservoir with fluid.

Example 10

The apparatus of Example 9, wherein the fluid conduit extends through a conduit opening disposed in the rigid body.

Example 11

The apparatus of Example 10, wherein the conduit opening and vent path are integral with each other.

Example 12

The apparatus of any one or more of Examples 10 through 11, wherein the conduit opening and the vent path are separately formed as discrete openings in the rigid body.

Example 13

The apparatus of any one or more of Examples 1 through 12, further comprising a flexible fluid conduit is fluidly coupled with the post, wherein the post is configured to communicate fluid from the fluid conduit to the nozzle head.

Example 14

The apparatus of any one or more of Examples 1 through 13, further comprising a pressure sensitive adhesive applied to the sealing element.

Example 15

The apparatus of Example 14, further comprising a liner strip, wherein the liner strip comprises a pair of attachment portions secured to the pressure sensitive adhesive on the sealing element.

Example 16

The apparatus of Example 15, wherein the sealing element defines an anterior zone, a posterior zone, a superior zone, and an inferior zone, wherein the attachment portions are configured to engage only the anterior and posterior zones of the sealing element, wherein the attachment portions are configured to not engage the superior and inferior zones of the sealing element.

Example 17

An apparatus, comprising: (a) an iontophoresis fluid reservoir, wherein the fluid reservoir defines a first volume; (b) a plug configured to define a closed volume in a patient's ear canal outside a tympanic membrane of the patient; (c) a working conduit configured to connect the iontophoresis fluid reservoir with the closed volume, wherein the working conduit defines a second volume; and (d) a drainage conduit passing from the fluid reservoir to a region outside the closed volume and plug; wherein the reservoir, plug, working conduit, and drainage conduit are configured to supply iontophoresis fluid through the working conduit, wherein the first volume of the fluid reservoir is greater than the second volume of the working conduit.

Example 18

An apparatus, comprising: (a) a plug configured to define a closed volume in a patient's ear canal outside a tympanic membrane of the patient, wherein the plug defines a channel configured to communicate with the closed volume, wherein the plug further includes a sealing element having a pressure sensitive adhesive thereon; (b) an iontophoresis electrode situated in the channel; and (c) a liner strip, wherein the liner strip comprises: (i) a pair of attachment portions, wherein each attachment portion is defined by a corresponding fold in the liner strip, wherein each attachment portion is configured cover two discrete portions the pressure sensitive adhesive on the sealing element, and (ii) a pair of gripping portions, wherein each gripping portion is defined by a fold in the liner strip, wherein each attachment portion is disposed on a distal end of a respective gripping portion.

Example 19

The apparatus of Example 18, wherein the attachment portions extend proximally from corresponding distal ends of the gripping portions.

Example 20

The iontophoresis apparatus of any one or more of Examples 18 through 19, wherein each attachment portion comprises a generally curved shape contoured to complement a curvature of the sealing element.

VI. MISCELLANEOUS

It should be understood that any of the examples described herein may include various other features in addition to or in lieu of those described above. By way of example only, any of the devices herein may also include one or more of the various features disclosed in any of the various references that are incorporated by reference herein. It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   a sealing element configured to form a seal with a surface of an ear canal to define a closed space within the ear canal adjacent to a tympanic membrane;
   a frame defining a channel, the sealing element coupled to a distal end of the frame;
   a nozzle coupled to a distal end of a tube, the tube extending through the channel, and the tube and the nozzle are configured to deliver a fluid including a therapeutic substance into the closed space; and
   an electrode disposed in the channel and circumscribing the tube, the electrode configured to deliver an electrorepulsive force to drive the therapeutic substance into the tympanic membrane;
   a vent path through the channel configured to enable air within the closed space to exit to an exterior of the apparatus when the nozzle delivers the fluid into the closed space, wherein the apparatus is configured to force air, responsive to the delivered fluid, through the channel, then through a reservoir, and then to the exterior of the apparatus.

2. The apparatus of claim 1, wherein the vent path is further configured to enable a portion of the fluid to exit the channel after the nozzle delivers an amount of fluid that fills a combined volume of the closed space and the channel.

3. The apparatus of claim 1, wherein the vent path is further configured to enable a portion of the fluid to exit to the channel in response to a change in volume of the closed space.

4. The apparatus of claim 1, further comprising a flexible fluid conduit that is fluidically coupled to a proximal end of the tube.

5. The apparatus of claim 1, wherein the electrode further comprises a coil of metallic material.

6. The apparatus of claim 1, further comprising:
   a pressure sensitive adhesive disposed on an outer surface of the sealing element and configured to provide a secure engagement between the sealing element and the surface of the ear canal; and
   a liner including a plurality of attachment portions, each attachment portion from the plurality of attachment portions configured to cover a respective portion of the outer surface of the sealing element with the pressure sensitive adhesive disposed thereon.

7. An apparatus, comprising:
   a flexible element;
   a housing comprising a channel defining a proximal end, a distal end, and the channel extending along a longitudinal central axis, the flexible element disposed at the distal end of the housing;
   a reservoir fluidically coupled to the proximal end of the channel;
   a fluid delivery assembly comprising a tube having a nozzle on the distal end of the tube, the tube extends through the channel parallel to the longitudinal central axis;
   an electrode disposed in the channel and at least partially circumscribing the tube of the fluid delivery assembly; and a vent associated with the reservoir and configured to enable air within the channel and the reservoir to exit to an exterior of the apparatus when the fluid delivery assembly delivers a fluid, wherein the apparatus is configured to force air, responsive to the delivered fluid, through the channel, then through the reservoir, and then to the exterior of the apparatus.

8. The apparatus of claim 7, wherein the vent is further configured to enable a portion of the fluid to exit to the reservoir.

9. The apparatus of claim 7, further comprising a flexible fluid conduit that is fluidically coupled to a proximal end of the tube.

10. A method, comprising:
inserting an earplug assembly into an ear canal such that a flexible element of the earplug assembly engages with a surface of the ear canal to define a closed space within the ear canal adjacent to a tympanic membrane;
delivering, via a fluid delivery path comprising a tube that extends through a channel defined by the earplug assembly, a fluid including a therapeutic substance into the closed space such that an electrode that at least partially circumscribes the fluid delivery path is submerged in the fluid;
venting air from the channel by way of a vent in operational relationship to the channel, wherein venting air comprises forcing air, responsive to the delivering of the fluid, through the channel, then through a reservoir, and then through the vent; and
providing, via the electrode, an electrorepulsive force to the fluid such that the therapeutic substance is delivered to the tympanic membrane.

11. The method of claim 10, wherein the reservoir is in fluid communication with the channel and the closed space, and the method further comprising venting, via the vent, a portion of the fluid outside the earplug assembly in response to a decrease in volume of the closed space.

12. The method of claim 10, wherein the providing the electrorepulsive force further comprises providing the electrorepulsive force by way of the electrode being a coil of metallic material circumscribing the tube of the fluid delivery path.

13. The method of claim 10:
wherein delivering the fluid further comprises delivering a volume of fluid greater than the closed space within the ear canal;
wherein venting air further comprises venting the air for a first portion of the delivering; and further comprising venting fluid from the channel by way of the vent when a volume of fluid delivered is greater than a volume of the closed space within the ear canal.

14. The method of claim 10, wherein inserting the earplug assembly further comprises removing a liner from a pressure sensitive adhesive disposed on an exterior surface of the flexible element.

* * * * *